US010633684B2

(12) United States Patent
Lehmann et al.

(10) Patent No.: US 10,633,684 B2
(45) Date of Patent: Apr. 28, 2020

(54) PRODUCTION OF RIBOFLAVIN

(75) Inventors: Martin Lehmann, Grenzach-Wyhlen (DE); Hans-Peter Hohmann, Loerrach (DE); Dietmar Laudert, Schopfheim (DE); Michael Hans, Schopfheim (DE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/127,618

(22) PCT Filed: Nov. 9, 2009

(86) PCT No.: PCT/EP2009/064825
§ 371 (c)(1),
(2), (4) Date: Aug. 31, 2011

(87) PCT Pub. No.: WO2010/052319
PCT Pub. Date: May 14, 2010

(65) Prior Publication Data
US 2011/0312025 A1    Dec. 22, 2011

(30) Foreign Application Priority Data

Nov. 7, 2008  (EP) .................................... 08019492

(51) Int. Cl.
| | |
|---|---|
| *C12Q 1/68* | (2018.01) |
| *C12P 25/00* | (2006.01) |
| *C12N 15/52* | (2006.01) |
| *C07K 14/32* | (2006.01) |

(52) U.S. Cl.
CPC .............. *C12P 25/00* (2013.01); *C07K 14/32* (2013.01); *C12N 15/52* (2013.01)

(58) Field of Classification Search
None
See application file for complete search history.

(56) References Cited

U.S. PATENT DOCUMENTS

| 5,474,796 A * | 12/1995 | Brennan ...................... 427/2.13 |
| 5,837,528 A | 11/1998 | Perkins et al. |
| 6,582,908 B2 * | 6/2003 | Fodor et al. ...................... 506/9 |
| 2003/0232406 A1 | 12/2003 | Perkins et al. |

FOREIGN PATENT DOCUMENTS

JP          3-117489          5/1991

OTHER PUBLICATIONS

Burgess et al. (Applied and environmental microbiology Oct. 2004 p. 5769) (Year: 2004).*
Mironov, A.S. et al., "Relationship between the secondary structure and the regulatory activity of the leader region of the riboflavin biosynthesis operon in Bacillus subtilis", Russian Journal of Genetics, vol. 44, No. 4, (Apr. 1, 2008), pp. 399-404.
Kreneva, R.A. et al., "Genetic mapping of regulatory mutations of Bacillus subtilis riboflavin operon", Molecular and General Genetics, vol. 222, No. 2-3, (Jul. 1, 1990), pp. 467-469.
Kil, Y.V. et al., "Riboflavin operon of *Bacillus subtilis:* unusual symmetric arrangement of the regulatory region", Mol. Gen. Cenet, (1992), pp. 483-486.
Vitreschak, A.G. et al., "Regulation of riboflavin biosynthesis and transport genes in bacteria by transcriptional and translational attenuation", Nucleic Acids Research, vol. 30, No. 14, (2002), pp. 3141-3151.
Mack, M. et al., "Regulation of Riboflavin Biosynthesis in *Bacillus subtilis* is affected by the Activity of the Flavokinase/Flavin Adenine Dinucleotide Synthetase Encoded by ribC", Journal of Bacteriology, vol. 180, No. 4, (Feb. 1998), pp. 950-955.
Mack et al, "Regulation of Riboflavin Biosynthesis in *Bacillus subtilis* is Affected by the Activity of the Flavokinase/Flavin Adenine Dinucleotide Synthetase Encoded by ribC", Journal of Bacteriology, Feb. 1998, vol. 180, No. 4, pp. 950-955.
Mironov et al, "Sensing Small Molecules by Nascent RNA: A Mechanism to Control Transcription in Bacteria", Cell, vol. 111, 747-756, Nov. 27, 2002.
Mironov et al, "Relationship between the Secondary Structure and the Regulatory Activity of the Leader Region of the Riboflavin Biosynthesis Operon in *Bacillus subtilis*", Russian Journal of Genetics, 2008, vol. 44, No. 4, pp. 399-404.
Humbelin et al, "Genetics of isoprenoid biosynthesis in *Paracoccus zeaxanthinifaciens*", Gene 297 (2002) 129-139.
Notice of Reasons for Rejection dated Apr. 1, 2014, issued in connection with Japanese Patent Application No. P2011-533772.

* cited by examiner

*Primary Examiner* — Katherine D Salmon
(74) *Attorney, Agent, or Firm* — Nixon & Vanderhye P.C.

(57) ABSTRACT

The present invention provides an improved biotechnological production of riboflavin (also referred herein as vitamin B2) through modification in the operon containing the riboflavin biosynthetic genes (rib operon), in particular modifications of/in the leader sequences (rib leader) upstream of the corresponding riboflavin biosynthetic genes (rib operon). Furthermore, the present invention relates to genetically engineered microorganisms carrying said modified sequences, processes to generate said modified sequences/microorganisms and the use thereof for production of riboflavin.

14 Claims, 8 Drawing Sheets

Specification includes a Sequence Listing.

```
1    acatattcccgttatgcatcgttatattaattatttacgagaatttacggttttttattc   60
61   atgaaaaaaaggaataactcatatgaatgaatagattcatattggctggaggtttagaaa  120
121  tgggaagaataaaaaccaagattaccattctgttagtgcttttgcttttacttgcaggcg  180
181  gttatatgtacataaatgatattgagctgaaggatgttccgacagcaattggacaaacct  240
241  tgtcctcggaagaagaggaatacaccatccaggaatataaagtgacgaaaattgacggct  300
301  cagagtatcatggagtagcagaaaacggaacgaaaatcatcttcaacggaaaaaaattaa  360
361  atcaggatttatctgatataaaagaaggtgacaagattaaggcttacttcagcaaatcaa  420
421  agcggatcgacggattaatcaaggttgcaaaagtgaatgattaaaaaacatcacctttcg  480
481  gatcgaagggtgatgttttgttttttctcaaattgtaagtttatttcattgcgtactttaa  540
541  aaaggatcgctataataaccaAtaaggacaaatgaataaagattgtatccttcggggcag  600
601  ggtggaaatcccgaccggcggtagtaaagcacatttgctttagagcccgtgacccgtgtg  660
661  cataagcacgcggtggattcagtttaagctgaagccgacagtgaaagtctggatgggaga  720
721  aggatgatgagccgctatgcaaaatgtttaaaaatgcatagtgttatttcctattgcgta  780
781  aaatacctaaagccccgaattttttataaattcggggcttttttgacggtaaataacaaa  840
841  agagggagggaaacaa atg 860
```

```
1    acatattcccgttatgcatcgttatattaattatttacgagaatttacggttttttattc  60
61   atgaaaaaaaggaataactcatatgaatgaatagattcatattggctggaggtttagaaa 120
121  tgggaagaataaaaaccaagattaccattctgttagtgcttttgcttttacttgcaggcg 180
181  gttatatgtacataaatgatattgagctgaaggatgttccgacagcaattggacaaacct 240
241  tgtcctcggaagaagaggaatacaccatccaggaatataaagtgacgaaaattgacggct 300
301  cagagtatcatggagtagcagaaaacggaacgaaaatcatcttcaacggaaaaaaattaa 360
361  atcaggatttatctgatataaaagaaggtgacaagattaaggcttacttcagcaaatcaa 420
421  agcggatcgacggattaatcaaggttgcaaaagtgaatgattaaaaaacatcacctttcg 480
481  gatcgaagggtgatgttttgttttctcaaattgtaagtttatttcattgcgtactttaa 540
                                                                A
541  aaaggatcgctataataaccaataaggacaaatgaataaagattgtatccttcggggcaG 600
     AA (triple ribO)                                  T (RK41)
601  GGtggaaatcccgaccggcggtagtaaagcacatttgctttagagCccgtgacccgtgtg 660
                            A (RK1a)
661  cataagcacgcggtggattcaGtttaagctgaagccgacagtgaaagtctggatgggaga 720
721  aggatgatgagccgctatgcaaaatgtttaaaaatgcatagtgttatttcctattgcgta 780
781  aaatacctaaagccccgaattttttataaattcggggcttttttgacggtaaataacaaa 840
841  agagggagggaaacaa atg 860
```

```
1    acatattcccgttatgcatcgttatattaattatttacgagaatttacggttttttattc  60
61   atgaaaaaaggaataactcatatgaatgaatagattcatattggctggaggtttagaaa   120
121  tgggaagaataaaaaccaagattaccattctgttagtgcttttgcttttacttgcaggcg  180
181  gttatatgtacataaatgatattgagctgaaggatgttccgacagcaattggacaaacct  240
241  tgtcctcggaagaagaggaatacaccatccaggaatataaagtgacgaaaattgacggct  300
301  cagagtatcatggagtagcagaaaacggaacgaaaatcatcttcaacggaaaaaattaa   360
361  atcaggatttatctgatataaaagaaggtgacaagattaaggcttacttcagcaaatcaa  420
421  agcggatcgacggattaatcaaggttgcaaaagtgaatgattaaaaaacatcacctttcg  480
481  gatcgaagggtgatgttttgttttctcaaattgtaagtttatttcattgcgtactttaa   540
541  aaaggatcgctataataaccataaggacaaatgaataaagattgtatccttcggggcag   600
601  ggtggaaatcccgaccggcggtagtaaagcacatttgctttagagcccgtgacccgtgtg  660
661  cataagcacgcggtggattcagtttaagctgaagccgacagtgaaagtctggatgggaga  720
721  aggatgatgagccgctatgcaaaatgtttaaaaatgcatagtgttatttcctattgcgta  780
781  aaatacctaaagccccgaatttttataaattcggggcttttttgacggtaaataacaaa   840
841  agagggagggaaacaa atg 860
```

D.

```
1    acatattcccgttatgcatcgttatattaattatttacgagaatttacggttttttattc  60
61   atgaaaaaaggaataactcatatgaatgaatagattcatattggctggaggtttagaaa   120
121  tgggaagaataaaaaccaagattaccattctgttagtgcttttgcttttacttgcaggcg  180
181  gttatatgtacataaatgatattgagctgaaggatgttccgacagcaattggacaaacct  240
241  tgtcctcggaagaagaggaatacaccatccaggaatataaagtgacgaaaattgacggct  300
301  cagagtatcatggagtagcagaaaacggaacgaaaatcatcttcaacggaaaaaattaa   360
361  atcaggatttatctgatataaaagaaggtgacaagattaaggcttacttcagcaaatcaa  420
421  agcggatcgacggattaatcaaggttgcaaaagtgaatgattaaaaaacatcacctttcg  480
481  gatcgaagggtgatgttttgttttctcaaattgtaagtttatttcattgcgtactttaa   540
541  aaaggatcgctataataaccataaggacaaatgaataaagattgtatccttcggggcag   600
601  ggtggaaatcccgaccggcggtagtaaagcacatttgctttagagcccgtgacccgtgtg  660
661  cataagcacgcggtggattcagtttaagctgaagccgacagtgaaagtctggatgggaga  720
721  aggatgatgagccgctatgcaaaatgtttaaaaatgcatagtgttatttcctattgcgta  780
781  aaatacctaaagccccgaatttttataaattcggggcttttttgacggtaaataacaaa   840
841  agagggagggaaacaa atg 860
```

```
1   acatattcccgttatgcatcgttatattaattatttacgagaatttacggttttttattc    60
61  atgaaaaaaggaataactcatatgaatgaatagattcatattggctggaggtttagaaa    120
121 tgggaagaataaaaaccaagattaccattctgttagtgcttttgcttttacttgcaggcg    180
181 gttatatgtacataaatgatattgagctgaaggatgttccgacagcaattggacaaacct    240
241 tgtcctcggaagaagaggaatacaccatccaggaatataaagtgacgaaaattgacggct    300
301 cagagtatcatggagtagcagaaaacggaacgaaaatcatcttcaacggaaaaaattaa    360
361 atcaggatttatctgatataaaagaaggtgacaagattaaggcttacttcagcaaatcaa   420
421 agcggatcgacggattaatcaaggttgcaaaagtgaatgattaaaaaacatcacctttcg   480
481 gatcgaagggtgatgttttgttttctcaaattgtaagtttatttcattgcgtactttaa    540
541 aaaggatcgctataataaccaataaggacaaatgaataaagattgtatccttcggggcag   600
601 ggtggaaatcccgaccggcggtagtaaagcacatttgctttagagcccgtgacccgtgtg   660
661 cataagcacgcggtggattcagtttaagctgaagccgacagtgaaagtctggatgggaga   720
721 aggatgatgagccgctatgcaaaatgtttaaaaatgcatagtgttatttcctattgcgta   780
781 aaatacctaaagccccgaattttttataaattcggggcttttttgacggtaaataacaaa   840
841 agagggagggaaacaa atg 860
```

F.

```
1   acatattcccgttatgcatcgttatattaattatttacgagaatttacggttttttattc    60
61  atgaaaaaaggaataactcatatgaatgaatagattcatattggctggaggtttagaaa    120
121 tgggaagaataaaaaccaagattaccattctgttagtgcttttgcttttacttgcaggcg    180
181 gttatatgtacataaatgatattgagctgaaggatgttccgacagcaattggacaaacct    240
241 tgtcctcggaagaagaggaatacaccatccaggaatataaagtgacgaaaattgacggct    300
301 cagagtatcatggagtagcagaaaacggaacgaaaatcatcttcaacggaaaaaattaa    360
361 atcaggatttatctgatataaaagaaggtgacaagattaaggcttacttcagcaaatcaa   420
421 agcggatcgacggattaatcaaggttgcaaaagtgaatgattaaaaaacatcacctttcg   480
481 gatcgaagggtgatgttttgttttctcaaattgtaagtttatttcattgcgtactttaa    540
541 aaaggatcgctataataaccaataaggacaaatgaataaagattgtatccttcggggcag   600
601 ggtggaaatcccgaccggcggtagtaaagcacatttgctttagagcccgtgacccgtgtg   660
661 cataagcacgcggtggattcagtttaagctgaagccgacagtgaaagtctggatgggaga   720
721 aggatgatgagccgctatgcaaaatgtttaaaaatgcatagtgttatttcctattgcgta   780
781 aaatacctaaagccccgaattttttataaattcggggcttttttgacggtaaataacaaa   840
841 agagggagggaaacaa atg 860
```

```
1   acatattcccgttatgcatcgttatattaattatttacgagaatttacggttttttattc   60
61  atgaaaaaaaggaataactcatatgaatgaatagattcatattggctggaggtttagaaa  120
121 tgggaagaataaaaaccaagattaccattctgttagtgcttttgcttttacttgcaggcg  180
181 gttatatgtacataaatgatattgagctgaaggatgttccgacagcaattggacaaacct  240
241 tgtcctcggaagaagaggaatacaccatccaggaatataaagtgacgaaaattgacggct  300
301 cagagtatcatggagtagcagaaaacggaacgaaaatcatcttcaacggaaaaaattaa   360
361 atcaggatttatctgatataaaagaaggtgacaagattaaggcttacttcagcaaatcaa  420
421 agcggatcgacggattaatcaaggttgcaaaagtgaatgattaaaaaacatcacctttcg  480
481 gatcgaagggtgatgttttgttttttctcaaattgtaagtttatttcattgcgtactttaa  540
541 aaaggatcgctataataaccaataaggacaaatgaataaagattgtatccttcggggcag   600
601 ggtggaaatcccgaccggcggtagtaaagcacatttgctttagagcccgtgacccgtgtg   660
661 cataagcacgcggtggattcagtttaagctgaagccgacagtgaaagtctggatgggaga   720
721 aggatgatgagccgctatgcaaaatgtttaaaaatgcatagtgttatttcctattgcgta   780
781 aaatacctaaagccccgaattttttataaattcggggcttttttgacggtaaataacaaa   840
841 agaggggagggaaacaa atg 860
```

H.

```
1   acatattcccgttatgcatcgttatattaattatttacgagaatttacggttttttattc   60
61  atgaaaaaaaggaataactcatatgaatgaatagattcatattggctggaggtttagaaa  120
121 tgggaagaataaaaaccaagattaccattctgttagtgcttttgcttttacttgcaggcg  180
181 gttatatgtacataaatgatattgagctgaaggatgttccgacagcaattggacaaacct  240
241 tgtcctcggaagaagaggaatacaccatccaggaatataaagtgacgaaaattgacggct  300
301 cagagtatcatggagtagcagaaaacggaacgaaaatcatcttcaacggaaaaaattaa   360
361 atcaggatttatctgatataaaagaaggtgacaagattaaggcttacttcagcaaatcaa  420
421 agcggatcgacggattaatcaaggttgcaaaagtgaatgattaaaaaacatcacctttcg  480
481 gatcgaagggtgatgttttgttttttctcaaattgtaagtttatttcattgcgtactttaa  540
541 aaaggatcgctataataaccaataaggacaaatgaataaagattgtatccttcggggcag   600
601 ggtggaaatcccgaccggcggtagtaaagcacatttgctttagagcccgtgacccgtgtg   660
661 cataagcacgcggtggattcagtttaagctgaagccgacagtgaaagtctggatgggaga   720
721 aggatgatgagccgctatgcaaaatgtttaaaaatgcatagtgttatttcctattgcgta   780
781 aaatacctaaagccccgaattttttataaattcggggcttttttgacggtaaataacaaa   840
841 agaggggagggaaacaa atg 860
```

```
1    acatattcccgttatgcatcgttatattaattatttacgagaatttacggttttttattc  60
61   atgaaaaaaggaataactcatatgaatgaatagattcatattggctggaggtttagaaa   120
121  tgggaagaataaaaaccaagattaccattctgttagtgcttttgcttttacttgcaggcg  180
181  gttatatgtacataaatgatattgagctgaaggatgttccgacagcaattggacaaacct  240
241  tgtcctcggaagaagaggaatacaccatccaggaatataaagtgacgaaaattgacggct  300
301  cagagtatcatggagtagcagaaaacggaacgaaaatcatcttcaacggaaaaaaattaa  360
361  atcaggatttatctgatataaaagaaggtgacaagattaaggcttacttcagcaaatcaa  420
421  agcggatcgacggattaatcaaggttgcaaaagtgaatgattaaaaaacatcacctttcg  480
481  gatcgaagggtgatgttttgttttctcaaattgtaagtttatttcattgcgtactttaa   540
541  aaaggatcgctataataaccaataaggacaaatgaataaagattgtatccttcggggcag  600
601  ggtggaaatcccgaccggcggtagtaaagcacatttgctttagagcccgtgacccgtgtg  660
661  cataagcacgcggtggattcagtttaagctgaagccgacagtgaaagtctggatgggaga  720
721  aggatgatgagccgctatgcaaaatgtttaaaaatgcatagtgttatttcctattgcgta  780
781  aaatacctaaagccccgaattttttataaattcggggcttttttgacggtaaataacaaa  840
841  agaggggagggaaacaa atg                                         860
```

A.

B.

SEQUENCE LISTING

<160> NUMBER OF SEQ ID NOS: 94

<210> SEQ ID NO 1
<211> LENGTH: 4230

```
<212> TYPE: DNA
<213> ORGANISM: Bacillus subtilis

<400> SEQUENCE: 1
taaggacaaa tgaataaaga ttgtatcctt cggggcaggg tggaaatccc gaccggcggt      60
agtaaagcac atttgcttta gagcccgtga cccgtgtgca taagcacgcg gtggattcag     120
tttaagctga agccgacagt gaaagtctgg atgggagaag gatgatgagc cgctatgcaa     180
aatgtttaaa aatgcatagt gttatttcct attgcgtaaa ataccta aag ccccgaattt     240 tttataaatt cggggctttt ttgacggtaa ataacaaaag aggggaggga acaaatgga      300 agagtattat atgaagctgg ccttagatct tgcgaagcag ggcgaaggac agaccgaatc     360
caatccgctc gtcggcgctg ttgtcgtaaa ggacggacaa attgtcggaa tgggcgccca     420
tttaaaatat ggtgaagctc atgcagaagt tcatgccatc catatggctg agcacatgc      480 agagggtgcc gacatttacg ttacactcga accgtgcagc cattacggaa aaacaccgcc     540
atgtgcagaa ttgattatca actctggtat caaaagagtg ttcgtggcga tgagagatcc     600
taatccgctt gtggctggaa gagggatcag catgatgaaa gaagctggca ttgaggtaag     660
ggaaggcatc ctggcagacc aggcggagag gctgaatgaa aaatttctgc actttatgag     720
gacaggcctt ccgtacgtca cgctaaaagc ggctgccagc cttgacggca agatagctac     780
cagcacgggt gacagcaaat ggatcacgtc agaggctgca agacaggatg ctcagcaata     840
caggaaaaca caccaaagca ttttagtcgg agttggcaca gtgaaagccg acaatccgag     900
cttaacctgc agactgccga atgtaacaaa acagccggtt cgggtcatac ttgataccgt     960
actctcgatt cctgaggacg ctaaagtgat ttgcgatcaa atagcgccga catggatttt    1020
tacgacggca cgcgcagacg aggaaaagaa aaaacggctt tcagcttccg gagtgaacat    1080
atttacactt gaaaccgagc gcattcaaat tcctgatgtt ttgaagatcc tagcggaaga    1140
aggcatcatg tcggtgtatg tggaaggcgg ttcagctgtt cacggaagct ttgtcaaaga    1200
aggctgtttt caagaaatca tcttctattt tgcccctaaa ctaatcggag gaacgcatgc    1260
tcccagctta atctccggtg aaggttttca atcaatgaaa gatgtcccct tattacaatt    1320
cactgatata acccaaatcg gccgtgatat caaactgacg gcaaaaccga caaaggaata    1380
ggatggtgac catgtttaca ggaattatcg aagaaacagg cacaatcgaa tccatgaaaa    1440
aagcagggca tgcaatggcc ttaactatta atgctcaaa gattttagag gatgttcatc     1500
ttggcgacag cattgcagtg aacggcattt gtctgactgt cactgatttt acaaaaaatc    1560
aattcacagt ggatgttatg cctgaaacag tcaaagctac gtcactgaat gatttaacaa    1620
aaggaagcaa agtaaatctg gaaagagcga tggcggcaaa cggccgtttc ggaggccatt    1680
tcgtctcagg ccatgtcgac ggaactgcgg aaatcacacg aattgaagag aaaagcaacg    1740
cagtttacta tgatttaaaa atggacccgt cattaacaaa acattggtt ttaaagggat     1800 caattactgt ggatggcgtg agcttaacca tattcggcct gacagaagac acagtgacga    1860
tctccttaat accgcatacg atcagcgaaa cgatctttc agaaaaaacg atcggctcta     1920
aagtgaatat cgaatgcgat atgatcgaa aatatatgta tcgattttg cataaagcca      1980 atgaaaataa gacccaacaa accattacaa aagccttctt aagcgaaaac ggcttttaga    2040
gaggaagatt tgcatgtttc atccgataga agaagcactg gacgctttaa aaaaaggcga    2100
agtcatcatc gttgtagatg atgaagacag agaaaatgaa ggagactttg tggctcttgc    2160
cgagcatgca acgccggaag tcattaactt tatggcgaca catgggagag gactgatctg    2220
```

| | |
|---|---|
| cacgccgctc agtgaggaaa tcgcagacag gcttgatctt caccctatgg ttgagcataa | 2280 |
| tacagactct caccacactg catttaccgt aagcatagac catcgtgaaa cgaagacagg | 2340 |
| tatcagcgct caagaaagat cttttaccgt tcaagcattg ctggacagca aatccgtgcc | 2400 |
| atctgatttt cagcgtccgg ggcacatttt tccactgatt gcgaaaaaag gaggtgtcct | 2460 |
| gaaaagagcg ggccatacag aagctgctgt tgatcttgct gaagcttgcg gatctccagg | 2520 |
| agccggcgtc atttgtgaaa ttatgaatga agacggaacg atggcgagag tgcctgagct | 2580 |
| cattgaaatt gcgaaaaagc atcaattaaa aatgatcacc attaaggatt tgattcaata | 2640 |
| ccgttacaat ctgacaacac ttgtcgagcg tgaagttgac attacgctgc ctactgattt | 2700 |
| tgggacattt aaggtttatg gatacacaaa tgaggtagat ggaaaagagc atgtcgcatt | 2760 |
| tgtgatggga gatgtgccgt tcggagaaga accggtattg gtccgggtgc attcagaatg | 2820 |
| tctcacaggt gacgtgtttg gctctcatcg ctgtgattgc ggaccgcagc tgcacgccgc | 2880 |
| gctgaaccaa attgccgcag aaggccgtgg agtgctcctg tacttgcgcc aagaaggacg | 2940 |
| aggcatcggt ttaatcaata aattaaaagc ttataagctt caggaacaag gctatgcacc | 3000 |
| cgtagaagcc aatgaggcgc ttggattctt gccggatctt cgcaactatg gcatcggagc | 3060 |
| acaaatttta cgcgaccctcg gtgtccggaa tatgaagctt ttgacgaata atccgcgaaa | 3120 |
| aatcgcaggc cttgaaggct acggactcag tatttcagaa agagtgccgc ttcaaatgga | 3180 |
| ggcgaaagaa cacaataaaa aatatttgca aaccaaaatg aacaagctag gtcatttact | 3240 |
| tcatttctaa tcacaaatat cacaaaaaag gatgggaatc atatgaatat catacaagga | 3300 |
| aatttagttg gtacaggtct taaaatcgga atcgtagtag gaagatttaa tgattttatt | 3360 |
| acgagcaagc tgctgagcgg agcagaagat gcgctgctca gacatggcgt agacacaaat | 3420 |
| gacattgatg tggcttgggt tccaggcgca tttgaaatac cgtttgctgc gaaaaaaatg | 3480 |
| gcggaaacaa aaaatatga tgctattatc acattgggca ctgtcatcag aggcgcaacg | 3540 |
| acacattacg attatgtctg caatgaagct gcaaaaggca tcgcgcaagc agcaaacact | 3600 |
| actggtgtac ctgtcatctt tggaattgta acaactgaaa acatcgaaca ggctatcgag | 3660 |
| cgtgccggca caaagcggg caacaaaggt gtagattgtg ctgtttctgc cattgaaatg | 3720 |
| gcaaatttaa accgctcatt tgaataattt gctgaaaaca gtttaaaaat atggcgaaaa | 3780 |
| tgatataatg tgagaaaacg gatcacctat tcgtatccgt taatagcaga ctggacatttt | 3840 |
| tggatataga ggggtttta tgttaattcg ttataaaaaa tcgtttgaaa agattgcgat | 3900 |
| ggggcttctt tcgtttatgc cgaatgaaaa agacctaag cagcttcagc agacaattaa | 3960 |
| ggactacgaa acggatacag accgccagct cttctttgg aaagaggacg aggatatcgt | 4020 |
| cggagcaatc ggagtcgaaa aaaaggattc tgaggttgag atccggcata tcagtgtgaa | 4080 |
| tccttctcat cgccatcaag gaatcggaaa acagatgatg gatgctttaa agcatttatt | 4140 |
| caaaacgcaa gtactggttc caaatgaatt aacgcagagc ttttcgaac gttgtcaagg | 4200 |
| tcagcaggat caagacattt catacaataa | 4230 |

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2
gcttgggctg caggtcgaga tc                                                    22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttcaaaatg gtatgcgttt tgacac                                                26

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatctcgacc tgcagcccaa gcgaaataaa cttacaattt gagaaaaac                       49

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acatattccc gttatgcatc g                                                     21

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgtcaaaac gcataccatt ttgaacgagt tggcacagtg aaagccg                         47

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctattccttt gtcggttttg ccg                                                   23

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatacctaaa gccccgaaga cggtaaataa caaaagagg                                  39

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttcggggctt taggtatttt acg                                          23

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctattgcgt aaaataccta aagacggtaa ataacaaaag ag                     42

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttaggtatt ttacgcaata ggaaataac                                    29

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taatttaaat tttatttgac aaaaatgggc tcgtgttgta caataaatgt agtgataagg  60
acaaatgaat aa                                                      72

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttgtcaaat aaaatttaaa ttagaaataa acttacaatt tgagaaaaac             50

<210> SEQ ID NO 14
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
taaaaatttt acaaaaaggt attgactttc cctacagggt gtgtaataat ttaattataa    60
ggacaaatga ataaagattg                                                80
```

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      primer <400> SEQUENCE: 15

```
caataccttt ttgtaaaatt tttagaaata aacttacaat ttgagaaaaa c             51
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer <400> SEQUENCE: 16

```
ccgtgacccg tgtgcataag c                                              21
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer <400> SEQUENCE: 17

```
aaatggaaat cccgaccggc ggtag                                          25
```

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer <400> SEQUENCE: 18

```
tatgcacacg ggtcacggac tctaaagcaa atgtgcttta c                        41
```

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      primer <400> SEQUENCE: 19

```
ctaccgccgg tcgggatttc cattttgccc cgaaggatac aatctttatt c             51
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer <400> SEQUENCE: 20
tttaagctga agccgacagt g                                              21

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtcggcttc agcttaaatt gaatccaccg cgtgctt                             37

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gccccgattt ttttataaat tttttgacgg taaataacaa aagagg                   46

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaaaattta taaaaaattc ggggctttag                                     30

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttaggtatt ttacgcaata gg                                             22

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctattgcgt aaaataccta aattttttat aaattcgggg cttttttg                 48

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
agtctggatg ggagaaggat ggacggtaaa taacaaaaga gg                42
```

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
cagtttaagc tgaagccatg ggacggtaaa taacaaaaga gg                42
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
catccttctc ccatccagac t                                       21
```

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ccatggcttc agcttaaact g                                       21
```

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      prime

<400> SEQUENCE: 30

```
ataattaaat tattacacac cctg                                    24
```

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
cagggtgtgt aataatttaa ttgacggtaa ataacaaaag agggg             45
```

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ttttaagtaa gtctactctg aatttttta gacggtaaat aacaaaagag ggg     53
```

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cagagtagac ttacttaaaa gactattctg caatctttat tcatttgtcc ttataa      56

<210> SEQ ID NO 34
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cctgtccttc tccttacact ttgagggagg tgaacacaga cggtaaataa caaaagaggg   60
g                                                                  61

<210> SEQ ID NO 35
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtgtaaggag aaggacaggt gctgcccttc gataaaatca atctttattc atttgtcctt   60
ataa                                                               64

<210> SEQ ID NO 36
<211> LENGTH: 8
<212> TYPE: DNA
<213> ORGANISM: Artificial Sequence
<220> FEATURE:
<223> OTHER INFORMATION: Description of Artificial Sequence: Synthetic
      "del stem loop-right" oligonucleotide

<400> SEQUENCE: 36 ttcggggc                                                            8

<210> SEQ ID NO 37
<211> LENGTH: 8
<212> TYPE: DNA
<213> ORGANISM: Artificial Sequence
<220> FEATURE:
<223> OTHER INFORMATION: Description of Artificial Sequence: Synthetic
      "del stem loop-left" oligonucleotide

<400> SEQUENCE: 37 gccccgaa                                                            8

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      "del flank-right" oligonucleotide

<400> SEQUENCE: 38 tttttttataa attcggggct ttttt                                         25

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      "del terminator" oligonucleotide

<400> SEQUENCE: 39
gccccgaatt ttttataaat tcggggcttt ttt                                 33

<210> SEQ ID NO 40
<211> LENGTH: 98
<212> TYPE: DNA
<213> ORGANISM: Artificial Sequence
<220> FEATURE:
<223> OTHER INFORMATION: Description of Artificial Sequence: Synthetic
      "SWITCH deletion" oligonucleotide

<400> SEQUENCE: 40
atgagccgct atgcaaaatg tttaaaaatg catagtgtta tttcctattg cgtaaaatac    60
ctaaagcccc gaattttttta taaattcggg gcttttttt                          98

<210> SEQ ID NO 41
<211> LENGTH: 128
<212> TYPE: DNA
<213> ORGANISM: Artificial Sequence
<220> FEATURE:
<223> OTHER INFORMATION: Description of Artificial Sequence: Synthetic
      "del mro175" oligonucleotide

<400> SEQUENCE: 41
gacagtgaaa gtctggatgg gagaaggatg atgagccgct atgcaaaatg tttaaaaatg    60
catagtgtta tttcctattg cgtaaaatac ctaaagcccc gaattttttta taaattcggg   120 gcttttttt                                                            128

<210> SEQ ID NO 42
<211> LENGTH: 263
<212> TYPE: DNA
<213> ORGANISM: Bacillus subtilis

<400> SEQUENCE: 42
ataaggacaa atgaataaag attgtatcct tcggggcagg gtggaaatcc cgaccggcgg    60
tagtaaagca catttgcttt agagcccgtg acccgtgtgc ataagcacgc ggtggattca   120
gtttaagctg aagccgacag tgaaagtctg gatgggagaa ggatgatgag ccgctatgca   180
aaatgtttaa aaatgcatag tgttatttcc tattgcgtaa aatacctaaa gccccgaatt   240
ttttataaat tcggggcttt ttt                                           263

<210> SEQ ID NO 43
<211> LENGTH: 41
<212> TYPE: DNA
<213> ORGANISM: Bacillus subtilis

<400> SEQUENCE: 43
acagaatagt cttttaagta agtctactct gaatttttt a                         41

<210> SEQ ID NO 44

```
<211> LENGTH: 57
<212> TYPE: DNA
<213> ORGANISM: Bacillus subtilis

<400> SEQUENCE: 44
attttatcga agggcagcac ctgtccttct ccttacactt tgagggaggt gaacaca        57

<210> SEQ ID NO 45
<211> LENGTH: 328
<212> TYPE: DNA
<213> ORGANISM: Bacillus subtilis

<400> SEQUENCE: 45
tttgtttttc tcaaattgta agtttatttc attgcgtact ttaaaaagga tcgctataat    60
aaccaataag gacaaatgaa taaagattgt atccttcggg gcagggtgga aatcccgacc   120
ggcggtagta aagcacattt gctttagagc ccgtgacccg tgtgcataag cacgcggtgg   180
attcaattta agctgaagcc gacagtgaaa gtctggatgg gagaaggatg atgagccgct   240
atgcaaaatg tttaaaaatg catagtgtta tttcctattg cgtaaaatac ctaaagcccc   300
gaatttttta taaattcggg gcttttttt                                     328

<210> SEQ ID NO 46
<211> LENGTH: 328
<212> TYPE: DNA
<213> ORGANISM: Bacillus subtilis

<400> SEQUENCE: 46
tttgtttttc tcaaattgta agtttatttc attgcgtact ttaaaaagga tcgctataat    60
aaccaataag gacaaatgaa taaagattgt atccttcggg gcagggtgga aatcccgacc   120
ggcggtagta aagcacattt gctttagagt ccgtgacccg tgtgcataag cacgcggtgg   180
attcagttta agctgaagcc gacagtgaaa gtctggatgg gagaaggatg atgagccgct   240
atgcaaaatg tttaaaaatg catagtgtta tttcctattg cgtaaaatac ctaaagcccc   300
gaatttttta taaattcggg gcttttttt                                     328

<210> SEQ ID NO 47
<211> LENGTH: 328
<212> TYPE: DNA
<213> ORGANISM: Bacillus subtilis

<400> SEQUENCE: 47
tttgtttttc tcaaattgta agtttatttc attgcgtact ttaaaaagga tcgctataat    60
aaccaataag gacaaatgaa taaagattgt atccttcggg gcaaatgga aatcccgacc    120 ggcggtagta aagcacattt gctttagagc ccgtgacccg tgtgcataag cacgcggtgg   180
attcagttta agctgaagcc gacagtgaaa gtctggatgg gagaaggatg atgagccgct   240
atgcaaaatg tttaaaaatg catagtgtta tttcctattg cgtaaaatac ctaaagcccc   300
gaatttttta taaattcggg gcttttttt                                     328

<210> SEQ ID NO 48
<211> LENGTH: 320
<212> TYPE: DNA
<213> ORGANISM: Bacillus subtilis

<400> SEQUENCE: 48
tttgtttttc tcaaattgta agtttatttc attgcgtact ttaaaaagga tcgctataat    60
aaccaataag gacaaatgaa taaagattgt atccttcggg gcagggtgga aatcccgacc   120
```

```
ggcggtagta aagcacattt gctttagagc ccgtgacccg tgtgcataag cacgcggtgg    180 attcagtttta agctgaagcc gacagtgaaa gtctggatgg gagaaggatg atgagccgct    240
atgcaaaatg tttaaaaatg catagtgtta tttcctattg cgtaaaatac ctaaagcccc    300 gaattttta taaattttt                                                   320

<210> SEQ ID NO 49
<211> LENGTH: 320
<212> TYPE: DNA
<213> ORGANISM: Bacillus subtilis

<400> SEQUENCE: 49 tttgttttc tcaaattgta agtttatttc attgcgtact ttaaaaagga tcgctataat    60
aaccaataag gacaaatgaa taaagattgt atccttcggg gcagggtgga aatcccgacc    120
ggcggtagta aagcacattt gctttagagc ccgtgacccg tgtgcataag cacgcggtgg    180
attcagttta agctgaagcc gacagtgaaa gtctggatgg gagaaggatg atgagccgct    240
atgcaaaatg tttaaaaatg catagtgtta tttcctattg cgtaaaatac ctaaatttt     300 tataaattcg gggctttttt                                                 320

<210> SEQ ID NO 50
<211> LENGTH: 303
<212> TYPE: DNA
<213> ORGANISM: Bacillus subtilis

<400> SEQUENCE: 50 tttgttttc tcaaattgta agtttatttc attgcgtact ttaaaaagga tcgctataat    60
aaccaataag gacaaatgaa taaagattgt atccttcggg gcagggtgga aatcccgacc    120
ggcggtagta aagcacattt gctttagagc ccgtgacccg tgtgcataag cacgcggtgg    180
attcagttta agctgaagcc gacagtgaaa gtctggatgg gagaaggatg atgagccgct    240
atgcaaaatg tttaaaaatg catagtgtta tttcctattg cgtaaaatac ctaaagcccc    300
gaa                                                                   303

<210> SEQ ID NO 51
<211> LENGTH: 295
<212> TYPE: DNA
<213> ORGANISM: Bacillus subtilis

<400> SEQUENCE: 51 tttgttttc tcaaattgta agtttatttc attgcgtact ttaaaaagga tcgctataat    60
aaccaataag gacaaatgaa taaagattgt atccttcggg gcagggtgga aatcccgacc    120
ggcggtagta aagcacattt gctttagagc ccgtgacccg tgtgcataag cacgcggtgg    180
attcagttta agctgaagcc gacagtgaaa gtctggatgg gagaaggatg atgagccgct    240
atgcaaaatg tttaaaaatg catagtgtta tttcctattg cgtaaaatac ctaaa         295

<210> SEQ ID NO 52
<211> LENGTH: 230
<212> TYPE: DNA
<213> ORGANISM: Bacillus subtilis

<400> SEQUENCE: 52 tttgttttc tcaaattgta agtttatttc attgcgtact ttaaaaagga tcgctataat    60
aaccaataag gacaaatgaa taaagattgt atccttcggg gcagggtgga aatcccgacc    120
```

```
ggcggtagta aagcacattt gctttagagc ccgtgacccg tgtgcataag cacgcggtgg    180
attcagttta agctgaagcc gacagtgaaa gtctggatgg gagaaggatg               230
```

<210> SEQ ID NO 53
<211> LENGTH: 204
<212> TYPE: DNA
<213> ORGANISM: Bacillus subtilis

<400> SEQUENCE: 53

```
tttgtttttc tcaaattgta agtttatttc attgcgtact ttaaaaagga tcgctataat    60
aaccaataag gacaaatgaa taaagattgg atccttcggg gcagggtgga aatcccgacc   120
ggcggtagta aagcacattt gctttagagc ccgtgacccg tgtgtataag cacgcggtgg   180
attcagttta agctgaagcc atgg                                          204
```

<210> SEQ ID NO 54
<211> LENGTH: 65
<212> TYPE: DNA
<213> ORGANISM: Bacillus subtilis

<400> SEQUENCE: 54

```
tttgtttttc tcaaattgta agtttatttc attgcgtact ttaaaaagga tcgctataat    60
aacca                                                                65
```

<210> SEQ ID NO 55
<211> LENGTH: 349
<212> TYPE: DNA
<213> ORGANISM: Bacillus subtilis

<400> SEQUENCE: 55

```
tttgtttttc tcaaattgta agtttatttc taaaaatttt acaaaaaggt attgactttc    60
cctacagggt gtgtaataat ttaattataa ggacaaatga ataaagattg tatccttcgg   120
ggcagggtgg aaatcccgac cggcggtagt aaagcacatt tgctttagag cccgtgaccc   180
gtgtgcataa gcacgcggtg gattcagttt aagctgaagc cgacagtgaa agtctggatg   240
ggagaaggat gatgagccgc tatgcaaaat gtttaaaaat gcatagtgtt atttcctatt   300
gcgtaaaata cctaaagccc cgaattttt ataaattcgg ggctttttt                349
```

<210> SEQ ID NO 56
<211> LENGTH: 347
<212> TYPE: DNA
<213> ORGANISM: Bacillus subtilis

<400> SEQUENCE: 56

```
tttgtttttc tcaaattgta agtttatttc taatttaaat tttatttgac aaaaatgggc    60
tcgtgttgta caataaatgt agtgataagg acaaatgaat aaagattgta tccttcgggg   120
cagggtggaa atcccgaccg gcggtagtaa agcacatttg ctttagagcc cgtgacccgt   180
gtgcataagc acgcggtgga ttcagtttaa gctgaagccg acagtgaaag tctggatggg   240
agaaggatga tgagccgcta tgcaaaatgt ttaaaaatgc atagtgttat tcctattgc    300 gtaaaatacc taaagccccg aattttttat aaattcgggg ctttttt                 347
```

<210> SEQ ID NO 57
<211> LENGTH: 347
<212> TYPE: DNA
<213> ORGANISM: Bacillus subtilis

<400> SEQUENCE: 57 tttgttttc tcaaattgta agtttatttc taatttaaat tttatttgac aaaaatgggc      60
tcgtgttgta caataaatgt agtgataagg acaaatgaat aaagattgga tccttcgggg    120
caaaatggaa atcccgaccg gcggtagtaa agcacatttg ctttagagcc cgtgacccgt    180
gtgcataagc acgcggtgga ttcagtttaa gctgaagccg acagtgaaag tctggatggg    240
agaaggatga tgagccgcta tgcaaaatgt ttaaaaatgc atagtgttat ttcctattgc    300
gtaaaatacc taaagccccg aatttttat aaattcgggg cttttttt                  347

```
<210> SEQ ID NO 58
<211> LENGTH: 347
<212> TYPE: DNA
<213> ORGANISM: Bacillus subtilis

<400> SEQUENCE: 58
``` tttgttttc tcaaattgta agtttatttc taatttaaat tttatttgac aaaaatgggc      60
tcgtgttgta caataaatgt agtgataagg acaaatgaat aaagattgta tccttcgggg    120
cagggtggaa atcccgaccg gcggtagtaa agcacatttg ctttagagtc cgtgacccgt    180
gtgcataagc acgcggtgga ttcagtttaa gctgaagccg acagtgaaag tctggatggg    240
agaaggatga tgagccgcta tgcaaaatgt ttaaaaatgc atagtgttat ttcctattgc    300
gtaaaatacc taaagccccg aatttttat aaattcgggg cttttttt                  347

```
<210> SEQ ID NO 59
<211> LENGTH: 349
<212> TYPE: DNA
<213> ORGANISM: Bacillus subtilis

<400> SEQUENCE: 59
``` tttgttttc tcaaattgta agtttatttc taaaaatttt acaaaaaggt attgactttc      60
cctacagggt gtgtaataat ttaattataa ggacaaatga ataaagattg tatccttcgg    120
ggcagggtgg aaatcccgac cggcggtagt aaagcacatt tgctttagag cccgtgaccc    180
gtgtgcataa gcacgcggtg gattcaattt aagctgaagc cgacagtgaa agtctggatg    240
ggagaaggat gatgagccgc tatgcaaaat gtttaaaaat gcatagtgtt atttcctatt    300
gcgtaaaata cctaaagccc cgaatttttt ataaattcgg ggcttttttt              349

```
<210> SEQ ID NO 60
<211> LENGTH: 328
<212> TYPE: DNA
<213> ORGANISM: Bacillus subtilis

<400> SEQUENCE: 60
``` tttgttttc tcaaattgta agtttatttc taatttaaat tttatttgac aaaaatgggc      60
tcgtgttgta caataaatgt agtgataagg acaaatgaat aaagattgta tccttcgggg    120
cagggtggaa atcccgaccg gcggtagtaa agcacatttg ctttagagcc cgtgacccgt    180
gtgcataagc acgcggtgga ttcaatttaa gctgaagccg acagtgaaag tctggatggg    240
agaaggatga tgagccgcta tgcaaaatgt ttaaaaatgc atagtgttat ttcctattgc    300
gtaaaatacc taaagccccg aatttttt                                       328

```
<210> SEQ ID NO 61
<211> LENGTH: 324
<212> TYPE: DNA
<213> ORGANISM: Bacillus subtilis
```

<400> SEQUENCE: 61

```
tttgttttcc tcaaattgta agtttatttc taaaaatttt acaaaaaggt attgactttc    60
cctacagggt gtgtaataat ttaattataa ggacaaatga ataaagattg tatccttcgg   120
ggcagggtgg aaatcccgac cggcggtagt aaagcacatt tgctttagag cccgtgaccc   180
gtgtgcataa gcacgcggtg gattcagttt aagctgaagc cgacagtgaa agtctggatg   240
ggagaaggat gatgagccgc tatgcaaaat gtttaaaaat gcatagtgtt atttcctatt   300
gcgtaaaata cctaaagccc cgaa                                          324
```

<210> SEQ ID NO 62
<211> LENGTH: 322
<212> TYPE: DNA
<213> ORGANISM: Bacillus subtilis

<400> SEQUENCE: 62

```
tttgttttcc tcaaattgta agtttatttc taatttaaat tttatttgac aaaaatgggc    60
tcgtgttgta caataaatgt agtgataagg acaaatgaat aaagattgta ccttcgggg   120
cagggtggaa atcccgaccg gcggtagtaa agcacatttg ctttagagcc cgtgacccgt   180
gtgcataagc acgcggtgga ttcagtttaa gctgaagccg acagtgaaag tctggatggg   240
agaaggatga tgagccgcta tgcaaaatgt ttaaaaatgc atagtgttat ttcctattgc   300
gtaaaatacc taaagccccg aa                                            322
```

<210> SEQ ID NO 63
<211> LENGTH: 316
<212> TYPE: DNA
<213> ORGANISM: Bacillus subtilis

<400> SEQUENCE: 63

```
tttgttttcc tcaaattgta agtttatttc taaaaatttt acaaaaaggt attgactttc    60
cctacagggt gtgtaataat ttaattataa ggacaaatga ataaagattg tatccttcgg   120
ggcagggtgg aaatcccgac cggcggtagt aaagcacatt tgctttagag cccgtgaccc   180
gtgtgcataa gcacgcggtg gattcagttt aagctgaagc cgacagtgaa agtctggatg   240
ggagaaggat gatgagccgc tatgcaaaat gtttaaaaat gcatagtgtt atttcctatt   300
gcgtaaaata cctaaa                                                   316
```

<210> SEQ ID NO 64
<211> LENGTH: 314
<212> TYPE: DNA
<213> ORGANISM: Bacillus subtilis

<400> SEQUENCE: 64

```
tttgttttcc tcaaattgta agtttatttc taatttaaat tttatttgac aaaaatgggc    60
tcgtgttgta caataaatgt agtgataagg acaaatgaat aaagattgta ccttcgggg   120
cagggtggaa atcccgaccg gcggtagtaa agcacatttg ctttagagcc cgtgacccgt   180
gtgcataagc acgcggtgga ttcagtttaa gctgaagccg acagtgaaag tctggatggg   240
agaaggatga tgagccgcta tgcaaaatgt ttaaaaatgc atagtgttat ttcctattgc   300
gtaaaatacc taaa                                                     314
```

<210> SEQ ID NO 65
<211> LENGTH: 251
<212> TYPE: DNA
<213> ORGANISM: Bacillus subtilis

<400> SEQUENCE: 65

```
tttgttttt tcaaattgta agtttatttc taaaaatttt acaaaaaggt attgactttc      60
cctacagggt gtgtaataat ttaattataa ggacaaatga ataaagattg tatccttcgg    120
ggcagggtgg aaatcccgac cggcggtagt aaagcacatt tgctttagag cccgtgaccc    180
gtgtgcataa gcacgcggtg gattcagttt aagctgaagc cgacagtgaa agtctggatg    240
ggagaaggat g                                                         251
```

<210> SEQ ID NO 66
<211> LENGTH: 86
<212> TYPE: DNA
<213> ORGANISM: Bacillus subtilis

<400> SEQUENCE: 66

```
tttgttttt tcaaattgta agtttatttc taaaaatttt acaaaaaggt attgactttc      60
cctacagggt gtgtaataat ttaatt                                          86
```

<210> SEQ ID NO 67
<211> LENGTH: 225
<212> TYPE: DNA
<213> ORGANISM: Bacillus subtilis

<400> SEQUENCE: 67

```
tttgttttt tcaaattgta agtttatttc taaaaatttt acaaaaaggt attgactttc      60
cctacagggt gtgtaataat ttaattataa ggacaaatga ataaagattg gatccttcgg    120
ggcaaaatgg aaatcccgac cggcggtagt aaagcacatt tgctttagag cccgtgaccc    180
gtgtgtataa gcacgcggtg gattcagttt aagctgaagc catgg                    225
```

<210> SEQ ID NO 68
<211> LENGTH: 223
<212> TYPE: DNA
<213> ORGANISM: Bacillus subtilis

<400> SEQUENCE: 68

```
tttgttttt tcaaattgta agtttatttc taatttaaat tttatttgac aaaaatgggc      60
tcgtgttgta caataaatgt agtgataagg acaaatgaat aaagattgga tccttcgggg    120
caaaatggaa atcccgaccg gcggtagtaa agcacatttg ctttagagcc cgtgacccgt    180
gtgtataagc acgcggtgga ttcagtttaa gctgaagcca tgg                      223
```

<210> SEQ ID NO 69
<211> LENGTH: 316
<212> TYPE: DNA
<213> ORGANISM: Bacillus subtilis

<400> SEQUENCE: 69

```
tttgttttt tcaaattgta agtttatttc taaaaatttt acaaaaaggt attgactttc      60
cctacagggt gtgtaataat ttaattataa ggacaaatga ataaagattg tatccttcgg    120
ggcagggtgg aaatcccgac cggcggtagt aaagcacatt tgctttagag tccgtgaccc    180
gtgtgcataa gcacgcggtg gattcagttt aagctgaagc cgacagtgaa agtctggatg    240
ggagaaggat gatgagccgc tatgcaaaat gtttaaaaat gcatagtgtt atttcctatt    300
gcgtaaaata cctaaa                                                    316
```

<210> SEQ ID NO 70

```
<211> LENGTH: 251
<212> TYPE: DNA
<213> ORGANISM: Bacillus subtilis

<400> SEQUENCE: 70 tttgttttc tcaaattgta agtttatttc taaaaatttt acaaaaaggt attgactttc      60
cctacagggt gtgtaataat ttaattataa ggacaaatga ataaagattg tatccttcgg    120
ggcagggtgg aaatcccgac cggcggtagt aaagcacatt tgctttagag tccgtgaccc    180
gtgtgcataa gcacgcggtg gattcagttt aagctgaagc cgacagtgaa agtctggatg    240
ggagaaggat g                                                         251

<210> SEQ ID NO 71
<211> LENGTH: 249
<212> TYPE: DNA
<213> ORGANISM: Bacillus subtilis

<400> SEQUENCE: 71 tttgttttc tcaaattgta agtttatttc taatttaaat tttatttgac aaaaatgggc      60
tcgtgttgta cataaaatgt agtgataagg acaaatgaat aaagattgta ccttcgggg    120 cagggtggaa atcccgaccg gcggtagtaa agcacatttg ctttagagtc cgtgacccgt    180
gtgcataagc acgcggtgga ttcagtttaa gctgaagccg acagtgaaag tctggatggg    240
agaaggatg                                                            249

<210> SEQ ID NO 72
<211> LENGTH: 186
<212> TYPE: DNA
<213> ORGANISM: Bacillus subtilis

<400> SEQUENCE: 72 tttgttttc tcaaattgta agtttatttc taaaaatttt acaaaaaggt attgactttc      60
cctacagggt gtgtaataat ttaattataa ggacaaatga ataaagattg cagaatagtc    120
ttttaagtaa gtctactctg aatttttta dacggtaaat aacaaaagag gggagggaaa    180
caaatg                                                               186

<210> SEQ ID NO 73
<211> LENGTH: 203
<212> TYPE: DNA
<213> ORGANISM: Bacillus subtilis

<400> SEQUENCE: 73 tttgttttc tcaaattgta agtttatttc taaaaatttt acaaaaaggt attgactttc      60
cctacagggt gtgtaataat ttaattataa ggacaaatga ataaagattg attttatcga    120
agggcagcac ctgtccttct ccttacactt tgagggaggt gaacacagac ggtaaataac    180
aaaagagggg agggaaacaa atg                                            203

<210> SEQ ID NO 74
<211> LENGTH: 263
<212> TYPE: DNA
<213> ORGANISM: Bacillus subtilis

<400> SEQUENCE: 74
ataaggacaa atgaataaag attgtatcct tcggggcagg gtggaaatcc cgaccggcgg     60
tagtaaagca catttgcttt agagcccgtg acccgtgtgc ataagcacgc ggtggattca    120
atttaagctg aagccgacag tgaaagtctg gatgggagaa ggatgatgag ccgctatgca    180
```

```
aaatgtttaa aaatgcatag tgttatttcc tattgcgtaa aatacctaaa gccccgaatt    240
ttttataaat tcggggcttt ttt                                            263

<210> SEQ ID NO 75
<211> LENGTH: 263
<212> TYPE: DNA
<213> ORGANISM: Bacillus subtilis

<400> SEQUENCE: 75
ataaggacaa atgaataaag attgtatcct tcggggcagg gtggaaatcc cgaccggcgg    60
tagtaaagca catttgcttt agagtccgtg acccgtgtgc ataagcacgc ggtggattca    120
gtttaagctg aagccgacag tgaaagtctg gatgggagaa ggatgatgag ccgctatgca    180
aaatgtttaa aaatgcatag tgttatttcc tattgcgtaa aatacctaaa gccccgaatt    240
ttttataaat tcggggcttt ttt                                            263

<210> SEQ ID NO 76
<211> LENGTH: 263
<212> TYPE: DNA
<213> ORGANISM: Bacillus subtilis

<400> SEQUENCE: 76
ataaggacaa atgaataaag attgtatcct tcggggcaaa atggaaatcc cgaccggcgg    60
tagtaaagca catttgcttt agagcccgtg acccgtgtgc ataagcacgc ggtggattca    120
gtttaagctg aagccgacag tgaaagtctg gatgggagaa ggatgatgag ccgctatgca    180
aaatgtttaa aaatgcatag tgttatttcc tattgcgtaa aatacctaaa gccccgaatt    240
ttttataaat tcggggcttt ttt                                            263

<210> SEQ ID NO 77
<211> LENGTH: 263
<212> TYPE: DNA
<213> ORGANISM: Bacillus subtilis

<400> SEQUENCE: 77
ataaggacaa atgaataaag attgtatcct tcggggcagg gtggaaatcc cgaccggcgg    60
tagtaaagca catttgcttt agagcccgtg acccgtgtgc ataagcacgc ggtggattca    120
gtttaagctg aagccgacag tgaaagtctg gatgggagaa ggatgatgag ccgctatgca    180
aaatgtttaa aaatgcatag tgttatttcc tattgcgtaa aatacctaaa gccccgaatt    240
ttttataaat tcggggcttt ttt                                            263

<210> SEQ ID NO 78
<211> LENGTH: 230
<212> TYPE: DNA
<213> ORGANISM: Bacillus subtilis

<400> SEQUENCE: 78
ataaggacaa atgaataaag attgtatcct tcggggcagg gtggaaatcc cgaccggcgg    60
tagtaaagca catttgcttt agagcccgtg acccgtgtgc ataagcacgc ggtggattca    120
gtttaagctg aagccgacag tgaaagtctg gatgggagaa ggatgatgag ccgctatgca    180
aaatgtttaa aaatgcatag tgttatttcc tattgcgtaa aatacctaaa                230

<210> SEQ ID NO 79
<211> LENGTH: 255
<212> TYPE: DNA
```

<213> ORGANISM: Bacillus subtilis

<400> SEQUENCE: 79

```
ataaggacaa atgaataaag attgtatcct tcggggcagg gtggaaatcc cgaccggcgg      60
tagtaaagca catttgcttt agagcccgtg acccgtgtgc ataagcacgc ggtggattca     120
gtttaagctg aagccgacag tgaaagtctg gatgggagaa ggatgatgag ccgctatgca     180
aaatgtttaa aaatgcatag tgttatttcc tattgcgtaa aatacctaaa gccccgaatt     240
ttttataaat ttttt                                                      255
```

<210> SEQ ID NO 80
<211> LENGTH: 255
<212> TYPE: DNA
<213> ORGANISM: Bacillus subtilis

<400> SEQUENCE: 80

```
ataaggacaa atgaataaag attgtatcct tcggggcagg gtggaaatcc cgaccggcgg      60
tagtaaagca catttgcttt agagcccgtg acccgtgtgc ataagcacgc ggtggattca     120
gtttaagctg aagccgacag tgaaagtctg gatgggagaa ggatgatgag ccgctatgca     180
aaatgtttaa aaatgcatag tgttatttcc tattgcgtaa aatacctaaa ttttttataa     240
attcggggct ttttt                                                      255
```

<210> SEQ ID NO 81
<211> LENGTH: 165
<212> TYPE: DNA
<213> ORGANISM: Bacillus subtilis

<400> SEQUENCE: 81

```
ataaggacaa atgaataaag attgtatcct tcggggcagg gtggaaatcc cgaccggcgg      60
tagtaaagca catttgcttt agagcccgtg acccgtgtgc ataagcacgc ggtggattca     120
gtttaagctg aagccgacag tgaaagtctg gatgggagaa ggatg                     165
```

<210> SEQ ID NO 82
<211> LENGTH: 135
<212> TYPE: DNA
<213> ORGANISM: Bacillus subtilis

<400> SEQUENCE: 82

```
ataaggacaa atgaataaag attgtatcct tcggggcagg gtggaaatcc cgaccggcgg      60
tagtaaagca catttgcttt agagcccgtg acccgtgtgc ataagcacgc ggtggattca     120
gtttaagctg aagcc                                                      135
```

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
gtagtaaagc acatttgctt tagagc                                           26
```

<210> SEQ ID NO 84
<211> LENGTH: 36
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 84
caaatgtgct ttactactgc cggtcgggat ttccac                               36

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gcggtagtaa agcacatttg c                                               21

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caaatgtgct ttactaccgc tggtcgggat ttccaccctg                           40

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tagtaaagca catttgcttt agagcc                                          26

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gctctaaagc aaatgtgctt tactatcgcc ggtcgggatt tccac                     45

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtgacccgtg tgcataagca c                                               21

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 90
tgcttatgca cacgggtcac aggctctaaa gcaaatgtgc tttac    45

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tgaagccgac agtgaaagtc tg    22

<210> SEQ ID NO 92
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gactttcact gtcggcttca acttaaactg aatccaccgc g    41

<210> SEQ ID NO 93
<211> LENGTH: 860
<212> TYPE: DNA
<213> ORGANISM: Bacillus subtilis

<400> SEQUENCE: 93
acatattccc gttatgcatc gttatattaa ttatttacga gaatttacgg ttttttattc    60
atgaaaaaaa ggaataactc atatgaatga atagattcat attggctgga ggtttagaaa   120
tgggaagaat aaaaaccaag attaccattc tgttagtgct tttgctttta cttgcaggcg   180
gttatatgta cataaatgat attgagctga aggatgttcc gacagcaatt ggacaaacct   240
tgtcctcgga agaagaggaa tacaccatcc aggaatataa agtgacgaaa attgacggct   300
cagagtatca tggagtagca gaaaacggaa cgaaaatcat cttcaacgga aaaaaattaa   360
atcaggattt atctgatata aaagaaggtg acaagattaa ggcttacttc agcaaatcaa   420
agcggatcga cggattaatc aaggttgcaa agtgaatga ttaaaaaaca tcacctttcg   480
gatcgaaggg tgatgttttg ttttctcaa attgtaagtt tatttcattg cgtactttaa   540
aaaggatcgc tataataacc aataaggaca aatgaataaa gattgtatcc ttcggggcag   600
ggtggaaatc ccgaccggcg gtagtaaagc acatttgctt tagagcccgt gacccgtgtg   660
cataagcacg cggtggattc agtttaagct gaagccgaca gtgaaagtct ggatgggaga   720
aggatgatga ccgctatgc aaaatgttta aaaatgcata gtgttatttc ctattgcgta   780
aaatacctaa agccccgaat ttttataaa ttcggggctt ttttgacggt aaataacaaa   840
agaggggagg gaaacaaatg                                                860

<210> SEQ ID NO 94
<211> LENGTH: 861
<212> TYPE: DNA
<213> ORGANISM: Bacillus subtilis

<400> SEQUENCE: 94
acatattccc gttatgcatc gttatattaa ttatttacga gaatttacgg ttttttattc    60

```
atgaaaaaaa ggaataactc atatgaatga atagattcat attggctgga ggtttagaaa        120
tgggaagaat aaaaaccaag attaccattc tgttagtgct tttgctttta cttgcaggcg        180
gttatatgta cataaatgat attgagctga aggatgttcc gacagcaatt ggacaaacct        240
tgtcctcgga agaagaggaa tacaccatcc aggaatataa agtgacgaaa attgacggct        300
cagagtatca tggagtagca gaaaacggaa cgaaaatcat cttcaacgga aaaaaattaa        360
atcaggattt atctgatata aaagaaggtg acaagattaa ggcttacttc agcaaatcaa        420
agcggatcga cggattaatc aaggttgcaa aagtgaatga ttaaaaaaca tcacctttcg        480
gatcgaaggg tgatgttttg ttttctcaa attgtaagtt tatttcattg cgtactttaa         540
aaaggatcgc tataataacc aataaggaca aatgaataaa gattgtatcc ttcggggcar        600
rrtggaaatc ccgaccggcg gtagtaaagc acatttgctt tagagyccgt gacccgtgtg        660
cataagcacg cggtggattc agrtttaagc tgaagccgac agtgaaagtc tggatgggag        720
aaggatgatg agccgctatg caaaatgttt aaaaatgcat agtgttattt cctattgcgt        780
aaaataccta aagccccgaa ttttttataa attcggggct tttttgacgg taaataacaa        840
aagaggggag ggaaacaaat g                                                  861
```

PRODUCTION OF RIBOFLAVIN

This application is the U.S. national phase of International Application No. PCT/EP2009/064825, filed 9 Nov. 2009, which designated the U.S. and claims priority to EP Application No. 08019492.1 filed 7 Nov. 2008, the entire contents of each of which are hereby incorporated by reference.

The present invention provides an improved biotechnological production of riboflavin (also referred herein as vitamin B2) through modification in the operon containing the riboflavin biosynthetic genes (rib operon), in particular modifications of/in the leader sequences (rib leader) upstream of the corresponding riboflavin biosynthetic genes (rib operon). Furthermore, the present invention relates to genetically engineered microorganisms carrying said modified sequences, processes to generate said modified sequences/microorganisms and the use thereof for production of riboflavin.

Riboflavin is synthesized by all plants and many microorganisms but is not produced by higher animals. Riboflavin is essential for basic metabolism, because it is a precursor of coenzymes such as flavin adenine dinucleotide and flavin mononucleotide that are required in the enzymatic oxidation of carbohydrates. In higher animals, insufficient riboflavin supply can cause loss of hair, inflammation of the skin, vision deterioration, and growth failure.

Biosynthesis of riboflavin starts from guanosine triphosphate (GTP) and ribulose-5-phosphate. The genes involved in biosynthesis of riboflavin are known from various sources, such as e.g., *Bacillus subtilis, Ereothecium ashbyii, Ashbya gossypii, Candida flareri, Saccharomyces cerevisiae, E. coli* (see e.g. EP 405370 or Ullman's Encyclopedia of Industrial Chemistry, 7$^{th}$ Edition, 2007, Chapter Vitamins).

With regards to the situation in *Bacillus subtilis* as one example of a riboflavin producing (micro)organism, the genes involved in riboflavin biosynthesis include ribG (ribD), ribB (ribE), ribA, and ribH. The ribA gene encodes two enzymatic activities, i.e. GTP cyclohydrolase II catalyzing the first step in riboflavin biosynthesis and 3,4-dihydroxy-2-butanone 4-phosphate synthase (DHBPS), which catalyzes the conversion of ribulose-5-phosphate to 3,4-dihydroxy-2-butanone 4-phosphate (DHBP). Deaminase and reductase are encoded by the first gene of the operon, ribG (ribD). The penultimate step in riboflavin biosynthesis is catalyzed by lumazine synthase, the gene product of ribH. Riboflavin synthase, which catalyzes the last step of the pathway, is encoded by the second gene of the operon, ribB (ribD). The function of ribT located at the 3' end of the rib operon is, at present, unclear; however, its gene product is not required for riboflavin synthesis.

Transcription of the riboflavin operon from the rib promoter ($P_{rib}$) is controlled by a riboswitch involving an untranslated regulatory leader region (hereinafter referred to as rib leader) of almost 300 nucleotides located in the 5' region of the rib operon between the transcription start and the translation start codon of the first gene in the operon, ribG. From studies using *Bacillus subtilis* it is known that at least three different parts within the rib leader are involved in transcriptional regulation of the rib operon: (i) a rho-independent terminator located at the 3'-end of the rib leader comprising an inverted repeat followed by a poly-T stretch characteristic for a rho-independent transcription termination or attenuation structure (Kil et al., Mol. Gen. Genet. 233, 483-486, 1992; Mironov et al., Mol. Biol. 24, 256-261, 1990); (ii) an inverted repeat at the 5'-half of the terminator suggested to function as antiterminator (Mironov et al., Cell 111, 747-756, 2002); (iii) two elements located in the middle part of the terminator and which are inverse complementary to each other presumed to act as an anti-antiterminator preventing the antiterminator to base pair with the terminator and to interfere with the formation of the antitermination structure (Mironov et al., Cell 111(5):747-56, 2002). It has been confirmed by in vitro transcription studies that the function of the terminator depends on the presence of FMN in the transcription assay (Winkler et al., PNAS 99(25): 15908-13, 2002). With regards to the rib operon of *B. subtilis* as depicted in e.g. SEQ ID NO:1, the terminator consists of nucleotides 230 to 263, the antiterminator consists of nucleotides 30 to 37, and the anti-antiterminator consists of nucleotides 157 to 164 of SEQ ID NO:1, respectively.

According to the current model of regulation of rib gene expression, the nascent mRNA transcribed from the rib leader adopts two alternative structures (so-called FMN riboswitch): if FMN is bound to the RFN element located within the rib leader (see e.g. the DNA sequence from position 25 to 164 in SEQ ID NO:1) the anti-antiterminator base-pairs with the antiterminator, which therefore can not interfere with the formation of the transcription termination loop resulting in premature termination of rib gene transcription. When no FMN is bound to the RFN element, the antiterminator base-pairs with the inverse complementary sequence of the transcription terminator allowing readthrough transcription and formation of full-length rib mRNA. This mechanism links the intracellular FMN concentration, which determines the ratio of FMN-bound RFN element to the unbound form, to the extent of full-length rib mRNA production. It has been shown that the RFN element only serves as binding site for FMN but not for riboflavin (Mironov et al, 2002; Winkler et al, 2002).

Accordingly, deregulation, riboflavin overproduction and secretion into the culture broth may be achieved by either (i) interfering with binding of FMN to the nascent mRNA transcribed from the rib leader sequence, (ii) modifying the anti-antiterminator such that it can not effectively base-pair with the antiterminator, or (iii) modifying or deleting the terminator.

One class of riboflavin-overproducing *B. subtilis* mutants identified contains single-point mutations, designated ribO mutations, at various positions in the 5'-half of the rib leader sequence (Kil et al., 1992). The ribO mutations are either located in the RFN element and thus interfere with FMN binding or are located in the anti-antiterminator DNA sequence. It can be expected that maximum deregulation of rib gene expression and riboflavin secretion is reached upon deletion of the terminator structure, since in this case the ultimate element, the repression of rib gene transcription depends on, is removed. RibO mutations have been furthermore identified in e.g. *Lactobacillus plantarum, Leuconostoc mesenteroides* or *Propionibacterium freudenreichii* (Burges et al., Microbial Cell Factories 5:24, 2006).

In a second class of riboflavin-overproducing *B. subtilis* mutants, designated ribC mutants, the chromosomal lesions were mapped at 147° of the *B. subtilis* genome (Kreneva and Perumov, Mol. Gen. Genet. 222, 467-469, 1990). RibC mutants contain missense mutations in the ribC gene. The ribC gene has been shown to encode the flavin kinase/FAD synthase of *B. subtilis* (Mack et al., J. Bacteriol., 180:950-955, 1998). Mutations deregulating riboflavin biosynthesis reduce the flavokinase activity of the ribC gene product resulting in reduced intracellular concentrations of flavin mononucleotide (FMN), the effector molecule of the riboflavin regulatory system.

Furthermore, classical mutagenesis was used to generate variants carrying random mutations in the genome of the organism of choice followed by e.g. selection for higher resistance to purine analogs. Alternatively, the genes involved in riboflavin biosynthesis were overexpressed through e.g. replacing the natural (weak) promoter by a strong promoter or amplification of expression cassettes within the chromosome, said cassettes containing a single promoter operably linked to gene(s) of interest together with an amplifiable selectable marker gene, e.g. an antibiotic resistance marker. The amplification led to the production of multiple copies of the expression cassette and the selectable marker gene in the chromosome. Additionally, increased secretion of riboflavin into the culture broth could be achieved by decoupling riboflavin production from the growth of said host cell.

Several disadvantages are associated with the above-mentioned approaches. For example, it may not be possible to achieve saturating levels of mRNA by amplification of genes driven by a single promoter. Furthermore, the production of multiple copies of the expression cassette and the selectable marker gene in the chromosome of a host cell may not be stable or might even prevent further expression of the respective gene (feedback inhibition).

Surprisingly, it has been discovered that the rib leader—besides its function as a negative regulator of rib gene expression as assumed by the current models—has a strong influence on the abundance of full-length rib mRNA, thus indicating a 5' mRNA stabilizing function. Introducing specific mutation(s)/deletion(s) into the rib leader sequence resulted in increased production of riboflavin.

Thus, it is an object of the present invention to improve the yields and/or productivity of riboflavin production by providing mutant riboflavin-producing strains wherein the rib leader has been modified in such a way that it leads to a relaxation or reduction of the repressive effect(s) on the expression of the consecutive rib gene(s) resulting in accumulation of intact, full-length rib mRNA transcript. Thus, the introduction of a modified rib leader, i.e. an improved rib leader compared to the wild-type rib leader, into a suitable host cell leads to higher transcription rates of consecutive rib genes, such as e.g. ribA, to higher stability of full-length rib mRNA and more deregulation of the rib operon, i.e. more deregulated riboflavin production.

In particular, it has been found that deletions at the 3' end of the rib leader including (i) the terminator sequences or functional parts thereof and (ii) 5' flanking regions of the terminator is specifically effective in improving the yield and/or productivity of riboflavin production. A modified rib leader wherein the entire DNA sequence from the 3' end of the RFN element to the 3' end of the terminator has been deleted is particularly useful in improving riboflavin production.

Furthermore, it has been found that the combination of ribO mutations together with deletions at the 3' end of the rib leader including the terminator sequences or functional parts thereof is specifically effective in improving the yield and/or productivity of riboflavin production. This could be even enhanced by including 5' flanking regions of the terminator. Unexpectedly, deletions or modifications of either the entire terminator sequence or functional parts thereof (without the combination with ribO mutations) have no strong effect on riboflavin production in contrast to larger deletions including the terminator together with 5' flanking regions or combinations of terminator deletions with ribO mutations. In fact, deletions or modifications of only the terminator sequence or functional parts thereof were clearly less effective in deregulating riboflavin production than classical ribO mutations. A modified rib leader wherein the entire DNA sequence from the 3' end of the RFN element to the 3' end of the terminator has been deleted in combination with one or more ribO mutations is particularly useful in improving riboflavin production. This could be even enhanced if larger parts of the RFN element are deleted, e.g., if approximately one-fifth of the 3' end of the RFN element are deleted.

Consequently, the present invention is directed to a modified or mutated polynucleotide selected from the group consisting of:
(a) polynucleotides comprising the nucleotide sequence according to SEQ ID NO:42,
(b) polynucleotides comprising a fragment or derivative of (a) having the activity of a rib leader,
(c) polynucleotides the complementary strand of which hybridizes under stringent conditions to a polynucleotide as defined in any one of (a) to (b) and have the activity of a rib leader,
(d) polynucleotides which are at least 70%, such as 80, 85, 90, 95 or 98% identical to a polynucleotide as defined in any one of (a) to (b) and which have the activity of a rib leader; and
(e) polynucleotides which are the complementary strand of a polynucleotide defined in (a) to (d);
wherein said polynucleotide, in particular the polynucleotide depicted under SEQ ID NO:42, comprises modification(s)/mutation(s) and wherein the accumulation of intact, full-length rib mRNA transcript is increased by at least 5% compared to a non-modified rib leader and furthermore leading to an increase in riboflavin production, said modification(s)/mutation(s) selected from the group consisting of:
(i) one or more mutation(s) at the 3' end of the rib leader including the terminator and 5' flanking regions thereof; and
(ii) one or more ribO mutation(s) together with one or more mutation(s) at the 3' end of the rib leader.

The non-modified rib leader as depicted in e.g. SEQ ID NO:42 may be part of a non-modified rib operon as e.g. shown in SEQ ID NO:1 isolated from *Bacillus subtilis*. The rib leader sequences as of the present invention may be used either with the natural rib promoter or with a constitutive promoter such as e.g. $P_{spo15}$ or $P_{veg}$ and as depicted in e.g. SEQ ID NO: 55 or 56.

The ribO mutations which are introduced into a rib leader and combined with modifications of the 3' end of the leader to result in the modified rib leader sequences as defined herein refer to any mutation(s) (base exchange, deletions, insertions) located at any position at the 5' end of the rib leader including the RFN element as defined/characterized by Kil et al., 1992 and which lead to improved riboflavin production compared to a strain carrying a non-modified rib leader as defined herein.

In particular, the invention relates to a modified rib leader which is modified in the 3' part and additionally contains one or more ribO mutations corresponding to the ones defined by Kil et al. (1992) or one or more, such as e.g. 1, 2, 3, 4, 5, 6, 7, 8, 9, 10, 11, 12, ribO mutations, i.e. substitution(s), on a position corresponding to a position as depicted in SEQ ID NO:42 which is selected from e.g. position 31, 39, 40, 41, 55, 85, 86, 88, 93, 116, 121, and 128. Preferably, the ribO mutation is selected from T31G, G39A, G40A, G41A, C55T, C85T, C86T, G88A, C93T, A116C, G121A, C128G, and combinations thereof wherein the nucleotides correspond to positions as depicted in SEQ ID NO:42. Examples of rib leader sequences carrying such ribO mutations including the natural rib promoter at the 5' end are shown in SEQ ID NOs:45, 46 and 47. These ribO mutations may be also fused to a constitutive promoter, such as e.g. $P_{veg}$ or $P_{spo15}$, depicted in e.g. SEQ ID NOs:57, 58 or 60 and SEQ ID NO:59, respectively. Preferably, the modified rib leader as defined herein comprises a single ribO mutation, such as e.g. located on a position corresponding to position 39, 40, 41, 85 or 121 as shown in SEQ ID NO:42, more preferably the ribO mutation is selected from G39A, G40A, G41A, C85T (named "RK41"), G121A (named "RK1a") and combinations thereof. Said ribO mutations are furthermore combined with mutation(s) in the 3' end of the rib leader as defined herein.

In a particular embodiment, a modified rib leader as of the present invention carries more than one ribO mutation combined with mutation(s) in the 3' end of the rib leader. Preferred is a combination of three ribO mutations, more preferably on a position corresponding to position 39, 40 and 41 of SEQ ID NO:42, even more preferably ribO mutations G39-G40A-G41A named "triple ribO". An example of such triple ribO mutation introduced into a rib leader is depicted in SEQ ID NO:47 (including the natural rib promoter). These ribO mutations may be also fused to a constitutive promoter by replacing the natural one, as depicted in e.g. SEQ ID NO:57.

Said ribO mutations are furthermore combined with modifications in the 3' end of the rib leader. Such modification in the 3' end of the rib leader may include at least deletion of the terminator or functional parts thereof to result in a modified rib leader as of the present invention which leads to increased production of riboflavin upon introduction into a suitable host cell compared to a host cell carrying a non-modified rib leader. Said modifications in the 3' end may furthermore include modifications, such as e.g. deletions, of 5' flanking regions of the terminator, in particular nucleotides corresponding to the 3' end of the RFN element, such as e.g. nucleotides corresponding to nucleotides 166 to 263 or 136 to 263 of SEQ ID NO:42.

In a preferred embodiment, the modification at/in the 3' end of the rib leader which is combined with ribO mutations as indicated above is located between the 3' end of the RFN element (i.e. all sequences which are located downstream of the RFN element) and the 3' end of the rib leader, wherein either the entire sequence may be deleted or only parts thereof. In one particular embodiment, the terminator or at least functional part thereof is included in said deletion.

An example of the terminator sequence as isolated from B. subtilis is depicted in SEQ ID NO:39 which might be deleted from the rib leader leading to a modified rib leader as shown in e.g. SEQ ID NOs:51 or 80, including the natural rib promoter. The natural promoter may also be replaced by a constitutive one, such as e.g. $P_{spo15}$ and $P_{veg}$ (see e.g. SEQ ID NOs:63 or 64). Thus, a modified rib leader as of the present invention may be deleted in nucleotides corresponding to nucleotides 231 to 263 of SEQ ID NO:42, i.e. deletion of the whole terminator (without flanking regions) named "del terminator" combined with any of the ribO mutations as defined above.

Deletion of functional parts of the terminator may include deletions of one or more stem loop(s) and/or flanking regions thereof. Examples of rib leader sequences wherein only functional parts of the terminator have been deleted combined with the above-specified ribO mutations are depicted in SEQ ID NOs:48, 49, 50, 77, 78, and 79. The natural rib promoter may also be replaced by a constitutive one, such as e.g. $P_{spo15}$ and $P_{veg}$ (see e.g. SEQ ID NOs:61 or 62). Taking the B. subtilis rib operon as depicted in SEQ ID NO:42 as a reference sequence, said functional part deletions may include deletions of nucleotides corresponding to nucleotides 250 to 257 named "del stem loop-right", nucleotides 231 to 238 named "del stem loop-left" or nucleotides 239 to 263 named "del flank-right".

Examples of modified rib leader sequences wherein the terminator and 5' flanking regions have been deleted combined with the above-specified ribO mutations are shown in SEQ ID NOs:52, 53, 81, and 82. The natural rib promoter may also be replaced by a constitutive one, such as e.g. $P_{spo15}$ and $P_{veg}$ (see e.g. SEQ ID NO:65). Taking the B. subtilis rib operon as depicted in SEQ ID NO:42 as a reference sequence, a modified rib leader as of the present invention may contain a deletion of nucleotides corresponding to nucleotides 166 to 263 of SEQ ID NO:42 named "SWITCH deletion" or corresponding to nucleotides 136 to 263 named "del mro175", which are combined with any of the above ribO mutations.

The modified rib leader sequences as described herein carry ribO mutations as defined above which are combined with mutation(s)/modification(s) in the 3' end of the rib leader, wherein the modifications in the 3' end may be selected from deletions of e.g. the complete terminator, functional parts of the terminator, or the terminator together with 5' flanking regions.

Furthermore, and as part of the invention, the modified rib leader sequences as defined herein carry mutation(s)/modification(s) in the 3' end of the rib leader, wherein the modifications may be selected from deletions of the terminator together with 5' flanking regions thereof, such as up to 60, 70, 80, 90 or 100 upstream of the terminator, in particular 64 or 94 nucleotides upstream, preferably nucleotides corresponding to nucleotides 166 to 263 or 136 to 263 of SEQ ID NO:42.

In one particular preferred embodiment, the host cell carrying the modified rib leader as defined above accumulates more than 25 mg/l riboflavin, such as 50, 100, 200, 300, 400, 500, 600, 700, 800 mg/l or more riboflavin, or even more than 1 g/l riboflavin in the culture medium compared to known ribO mutants as defined by Kil et al. (1992), such as e.g. ribO mutations T31G, G39A, G40A, G41A, C55T, C85T, C86T, G88A, C93T, A116C, G121A, C128G, and combinations thereof wherein the nucleotides correspond to positions as depicted in SEQ ID NO:42. The skilled person knows that these amounts vary depending on e.g. culture conditions, host strain and/or substrate.

In one embodiment, a modified rib leader as of the present invention contains a ribO mutation corresponding to ribO mutation selected from RK1a, RK41 or triple ribO in the B. subtilis rib operon (SEQ ID NO:42) combined with a 3' end deletion selected from deletion of the whole terminator, a SWITCH deletion or del mro175 (see above). A preferred combination is RK1a with del terminator, SWITCH deletion, or del mro175. Also preferred is the combination of RK41 with del terminator, SWITCH deletion, or del mro175. Furthermore preferred is the combination of triple ribO with del terminator, SWITCH deletion, or del mro175. More preferably, the modified rib leader as of the present invention contains a combination of RK41 with del terminator, RK41 with SWITCH deletion, triple ribO with del mro175. Even more preferred are said modified rib leader sequences fused to constitutive promoter such as e.g. $P_{spo15}$ and $P_{veg}$ (see e.g. SEQ ID NOs:67, 68, 69, 70 or 71).

A modified rib leader according to the present invention may also include modifications via the introduction of mRNA stabilizing elements. Said elements may be introduced between the promoter and the coding sequences of the rib gene(s). Examples of such elements include the ones shown in SEQ ID NO:43 (so-called aprE mRNA stabilizing element) or SEQ ID NO:44 (so-called grpE mRNA stabilizing element) and sequences hybridizing under preferably highly stringent conditions thereto.

The nucleic acid sequences, i.e. modified rib leader sequences, as of the present invention may be operatively linked to an appropriate promoter, which may be either a constitutive or inducible promoter. The promoter will be either the natural one or a promoter which is originally not naturally linked to the respective gene(s) involved in biosynthesis of riboflavin. The skilled person will know how to select suitable promoters. Examples of useful promoters can be found in the literature, see in particular, e.g. EP 405370.

Thus, the invention relates in a preferred embodiment to a modified or mutated polynucleotide (rib leader sequence) selected from the group consisting of:
(a) polynucleotides comprising the (modified) nucleotide sequence according to SEQ ID NOs:65, 67, 68, 69, 70 or 71;
(b) polynucleotides the complementary strand of which hybridizes under stringent conditions to a polynucleotide as defined in (a) and have the activity of a modified rib leader,
(c) polynucleotides which are at least 70%, such as 80, 85, 90, 95 or 98% identical to a polynucleotide as defined in (a) and which have the activity of a modified rib leader; and
(d) polynucleotides which are the complementary strand of a polynucleotide defined in (a) to (c);
wherein said polynucleotides, in particular the sequences depicted under SEQ ID NOs:65, 67, 68, 69, 70 or 71, are referred to as modified or mutated sequences wherein the accumulation of intact, full-length rib mRNA transcript is increased by at least 5% upon introduction into a suitable host cell compared to a cell carrying the corresponding non-modified sequences.

As used herein, the term "rib leader sequence" refers to any DNA sequence that is associated with one or more downstream rib gene(s) and that contains untranslated regulatory elements, which affect expression of the consecutive rib gene(s). These regulatory elements typically comprise (i) a terminator at the 3' end of the DNA sequence, (ii) an anti-terminator, and (iii) an RFN binding site upstream of the terminator. As known from *Bacillus subtilis*, the rib leader encompasses almost 300 nucleotides located in the 5' region of the rib operon between the transcription start and the translation start codon of the first gene in the operon, ribG. The terminator sequence in the rib leader of *B. subtilis* is located between nucleotides 231 and 263 (see FIG. 1). Such rib leader sequences have been furthermore identified in other eubacteria such as *Bacillus*, *Corynebacterium*, *Pseudomonas* in particular *B. anthracis, B. cereus, B. stearothermophilus, B. halodurans, B. amyloliquefaciens, C. diphteriae* and *C. glutamicum, P. aeroginosa, P. putida* or *P. syringiae* (see Table 1 of Vitreschak et al., Nucleic Acid Res 30, 3141-3151, 2002 and which is incorporated herein as reference).

The term "RFN element" as used herein refers to highly conserved DNA sequences within a rib leader sequence. After transcription into mRNA the RFN elements can fold into conserved structures with five hairpins forming a binding site for FMN. Potential RFN elements can be identified using RFAM, which is a collection of multiple sequence alignments and covariance models representing non-coding RNA families (Griffiths-Jones et al.: Rfam: an RNA family database. Nucleic Acids Res 2003, 31:439-441; available at http://www.sanger.ac.uk/cgi-bin/Rfam/getacc?RF00050).

Examples of RFN elements in the genomes of various bacteria are provided by Gelfand et al., Trends Genet. 15, 439-442, 1999. An overview including the nucleotide sequences of RFN elements from different organisms is given in FIG. 2 of Vitreschak et al., Nucleic Acid Res 30, 3141-3151, 2002. According to the definition of Mironow et al., Cell 111(5):747-56, 2002 the RFN element within the rib leader sequence of *B. subtilis* is located between nucleotides 22 to 165 (see FIG. 1 or SEQ ID NO:42). With the help of the alignment shown in FIG. 2 of Vitreschak et al., 2002 the skilled person is able to generate modified rib leader in organisms containing such an RFN element leading to increased riboflavin production.

The term "non-modified rib leader" or "non-modified polynucleotide" and "wild-type rib leader" or "wild-type polynucleotide" are used interchangeably herein. Non-modified rib leader or non-modified polynucleotides may include any polynucleotide that hybridizes preferably under highly stringent conditions to a sequence shown in SEQ ID NO:42 for which increasing the specific activity is desirable in order to relieve the repressive effects of the rib leader, to increase stability of rib gene mRNA, to lead to a more deregulated rib operon and/or to increase production of riboflavin in a given microorganism. These sequences are then used as starting point for designing mutant rib leader sequences with increased activity according to the present invention. "Wild-type" in the context of the present invention may include both sequences derivable from nature as well as variants of synthetic sequences, if they can be made more active by any of the teachings of the present invention. In particular, such polynucleotides are of prokaryotic origin, preferably bacterial origin, in particular originated from Gram positive or Gram negative bacteria, e.g. *Bacillus*, preferably *Bacillus subtilis*.

The terms "modified polynucleotide" or "modified rib leader" and "mutant polynucleotide" or "mutant rib leader" are used interchangeably herein. A mutant/modified polynucleotide or modified rib leader may include any variant derivable from a given wild-type polynucleotide/rib leader (according to the above definition) according to the teachings of the present invention and being more active (such as e.g. measurable as increase in riboflavin produced from a given substrate or as increased rib mRNA stability) than the respective wild-type sequence. For the scope of the present invention, it is not relevant how the mutant(s) are obtained; such mutants may be obtained, e.g., by site-directed mutagenesis, saturation mutagenesis, random mutagenesis/directed evolution, chemical or UV mutagenesis of entire cells/organisms, and other methods which are known in the art. These mutants may also be generated, e.g., by designing synthetic genes. The modifications in the rib leader sequence and their effect on expression of the rib genes can be measured by methods known to those skilled in the art. For instance, these methods include assays using beta-galactosidase as reporter gene or secretion of riboflavin into the culture broth of microorganisms containing the modified rib leader sequence instead of or in addition to the wild-type rib leader sequence. The (positive) effect of modified rib leaders on the respective mRNA levels may also be determined via Northern blots or real-time PCR.

The skilled person knows how to generate mutated/modified rib leader sequences including introduction of mRNA stabilizing elements and/or replacement of the natural promoter. In one embodiment, a modified rib leader is generated via the introduction of mRNA stabilizing elements into a previously non-modified rib leader. An example of a useful method for the introduction of such mRNA stabilizing elements is shown in FIG. 2.

Said generation of mutated/modified rib leader sequences may for instance be accomplished by either genetically modifying the host organism in a way as described herein that it produces a mutated rib leader wherein the repressive effect(s) on rib gene expression has been relaxed or reduced compared to a non-modified rib leader, which in turn leads to increased accumulation of intact, full-length rib mRNA transcripts and thus to an increase in efficiency and/or yield of riboflavin production. Thus, with a modified rib leader the rib operon is less regulated or more deregulated compared to a strain carrying a non-modified rib leader.

"Improved activity" or "enhanced activity" as used herein is to be understood as a relaxation (totally or partial) or reduction of repressive effect(s)/reduction of regulation of the rib leader in a riboflavin producing microorganism. Thus, for the purpose of the present invention, a modified rib leader with increased activity has less repressive influence on the transcription of rib genes leading to deregulation of the rib operon compared to a non-modified rib leader. Furthermore, a modified rib leader with improved activity as defined herein leads to an accumulation of intact, full-length rib mRNA which is increased by at least 5%, 10%, 25%, 50%, 75%, 100%, 200% or even more than 500% as determined by Northern blot or real-time PCR. This can be measured (indirectly) via an increase in riboflavin production upon minimized repression/regulation of the rib leader or via determination of the mRNA concentration of full-length transcripts or concentration of riboflavin biosynthetic enzymes transcribed from the rib genes. A modified rib leader is at least 5%, 10%, 25%, 50%, 75%, 100%, 200% or even more than 500% less repressive/regulated on rib gene expression compared to a wild-type rib leader. Thus, a modified rib leader having improved activity refers to a rib leader with a level of deregulation which is increased by at least 5%, 10%, 25%, 50%, 75%, 100%, 200% or even more than 500% compared to a non-modified rib leader as defined herein.

The term "mRNA stabilizing element" as used herein refers to a DNA sequence which upon introduction in the 5'-untranslated region, e.g. downstream of the transcription start of the respective gene, is capable of providing an increased stability to the mRNA which is transcribed from the respective gene comprising said mRNA stabilizing element. The mRNA stabilizing element preferably contains 1 or more stem loops but may also contain no stem loop at all.

Any nucleic acid sequence capable of forming one or more stem loop(s) leading to increased stability of mRNA transcripts from one or more target gene(s) which are preferably involved in the production of riboflavin may be within the scope of the present invention. Stabilization of mRNA may also be possible via a strong ribosome binding site (RBS) which does not necessarily form a loop.

The mRNA stabilizing elements as defined above may be of any length but preferably consist of at least 15 nucleotides, more preferably at least 20, 30, 40, 50, 60, 70, 80, 90, 100 nucleotides, most preferably 39-87 nucleotides comprising preferably 1 or more stem loops, in particular 1 or 2 stem loops. The stem may consist of at least 4 base pairs, preferably at least 8, 10, 12, 15 base pairs (with mismatch nucleotides/interior loops and/or bulge loops possibly being present) and the loops may consist of e.g. 3-30 unbounded nucleotides, preferably 4, 6, 8, 10, 11, 14, 15, 25 or more nucleotides. The length of the interior loops is preferably 2, 4, 6, 8, 10, 12 unbounded nucleotides. One or more bulge loop(s) may be present, consisting of e.g. 1, 2 or even 6 unbounded nucleotides. The calculated thermodynamic stability ($\Delta G$) of the stem loop may be calculated according to algorithms developed by Zuker (2003, Nucleic Acids Res. 31:3406-3415). In one embodiment, the calculated thermodynamic stability is $-2.8$ kcal/mol or lower, preferably $-3$, $-4$, $-5$, $-6$, $-7$, $-8$, $-9$, $-10$, $-11$, $-12$, $-15$, $-20$ kcal/mol or lower. In another embodiment of the present invention, the mRNA stabilizing elements may comprise no loop at all.

The stability or integrity of rib mRNA transcripts may be for instance measured by determination of the mRNA half-life using Northern blot and/or real-time PCR stabilization as described e.g. by Allenby et al., Microbiology, 150, p. 2619-2628 (2004) or Sharp and Bechhofer, Mol. Microbiol. 57, 484-495 (2005). As used herein, the mRNA stability or integrity is increased (or mRNA degradation is reduced/blocked) if the half-life of said mRNA is increased by at least 1%, 2%, 5%, 10%, 25%, 50%, 75%, 100%, 200% or even more than 500%, compared to mRNA half-life transcribed from a wild-type rib operon, i.e. not containing a modified rib leader as of the present invention.

The template DNA may be derived from the same or a different host cell to be used for the production of riboflavin. Furthermore, the template for the reaction may be cDNA obtained by reverse transcription of mRNA prepared from strains known or suspected to comprise a polynucleotide according to the invention. The PCR product may be sub-cloned and sequenced to ensure that the amplified sequences represent the sequences of a new nucleic acid sequence as described herein, or a functional equivalent thereof. Furthermore, a nucleic acid sequence according to the present invention may be completely or partly synthesized using methods well-known in the art.

The invention also relates to polynucleotides (rib leader sequences) and their use for the production of riboflavin the complementary strand of which hybridizes under stringent conditions to a polynucleotide as defined herein and which are able to improve the accumulation of intact, full-length rib mRNA transcripts.

The invention also relates to polynucleotides and their use for the production of riboflavin, said polynucleotides being at least 70% identical to a polynucleotide as defined herein and have the activity of a modified rib leader. In one embodiment, a nucleic acid of the invention is at least 70%, 75%, 80%, 85%, 90%, 91%, 92%, 93%, 94%, 95%, 96%, 97%, 98%, 99%, or more identical to a polynucleotide shown in SEQ ID NO:42, 55, 56, 67, 68, 69, 70, 71, or the complement thereof.

The invention also relates to primers, probes and fragments that may be used to amplify or detect a DNA according to the invention and to identify relating species or families of microorganisms also carrying such rib leader sequences.

The invention also relates to vectors which include polynucleotides of the invention and microorganisms which are genetically engineered with the polynucleotides or said vectors.

The invention also relates to processes for generating microorganisms carrying modified polynucleotides as defined herein, i.e. genetically engineering a suitable microorganism in order to increase the accumulation of intact, full-length rib mRNA transcripts, and their use for improving and/or enhancing the yield and/or efficiency of riboflavin production.

Introduction of a DNA sequence as used herein may be for instance addition or insertion of a DNA sequence by transformation, conjugation or transduction into the chromosome of a host cell. Said addition or insertion may occur by DNA recombination that may or may not also result in a removal or deletion of chromosomal DNA nucleotides. Methods by which introduction of DNA sequences into a host cell, e.g. microorganisms, are achieved, especially by site-specific introduction, are well-known in the art and described in e.g. Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Suitable host cells include cells of microorganisms capable of producing riboflavin, e.g. converting a given carbon source into riboflavin and which carry either a non-modified rib operon including a non-modified leader or equivalent or homologue thereof (which is then mutated in such a way that it leads to an increase in riboflavin production as described herein) or into which a modified version of said rib operon/rib leader or equivalent thereof is introduced. Such cell is then called "recombinant cell" or "transformed cell". Suitable microorganisms carrying such a non-modified rib operon/rib leader or equivalent thereof may be selected from bacteria, such as e.g. Gram-negative and Gram-positive bacteria, either as wild-type strains, mutant strains derived by classical mutagenesis and selection methods or as recombinant strains. Suitable strains carrying RFN elements are listed in Table 1 and FIG. 2 of Vitreschak et al., Nucleic Acid Res 30, 3141-3151, 2002. Examples of such bacteria include *Bacillus, Streptococcus, Lactococcus, Streptomyces, Clostridium, Deionococcus, Thermus, Fusobacterium, Chloroflexus* and *Thermomonospora*. Preferably, the microorganism or host cell is selected from the group consisting of *Bacillus subtilis, Bacillus cereus, Bacillus amyloliquefaciens, Bacillus stearothermophilus, Bacillus halodurans, Bacillus lichenifonnis* and *Streptococcus aureus, Streptococcus pneumoniae, Clostridium acetobutylicum, Clostridium difficile, Lactococcus lactis* or of less related organisms like *Streptomyces coelicolor, Thermomonospora fusca, Deionococcus radiodurans, Thermus thermophilus, Thermotoga maritima, Fusobacterium nucleatum*, and *Chloroflexus aurantiacus*. More preferred is *B. subtilis*, in particular *B. subtilis* 1A747 or *B. subtilis* 168. It is also in the scope of this invention that a deregulated/modified rib leader from e.g. *B. subtilis* as disclosed herein is used to replace the native/wild-type rib leader in one of the other microorganisms mentioned above or that a modified rib leader of another organism mentioned above is used in front of the rib operon of *B. subtilis*.

Such a microorganism carrying said modified rib leader are also referred to as genetically modified or recombinant microorganisms or recombinantly produced/genetically engineered host cells.

Microorganisms which can be used for the present invention may be publicly available from different sources, e.g., Deutsche Sammlung von Mikroorganismen und Zellkulturen (DSMZ), Inhoffenstrasse 7B, D-38124 Braunschweig, Germany, American Type Culture Collection (ATCC), P.O. Box 1549, Manassas, Va. 20108 USA, Agricultural Research Culture Collection (NRRL), Peoria, Ill., USA, Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan) or the *Bacillus* Genetic Stock Center (BGSC), The Ohio State University, Columbus, Ohio 43210 USA.

In connection with the present invention it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM).

The present invention is directed to modified microorganisms, wherein said modification leads to an increased yield, production and/or efficiency of riboflavin from substrates like e.g. glucose. This may be performed by increasing the activity of the rib leader as described herein, i.e. decreasing the level of regulation. In addition, a microorganism as of the present invention may carry further modifications as long as such modification has a direct impact on the yield, production and/or efficiency of riboflavin production.

Thus, in one embodiment the present invention is directed to a microorganism carrying a modified rib leader as described herein and additional modification(s), such as e.g. by replacing the natural promoter of the rib operon by a strong (constitutive or inducible) promoter such as e.g. $P_{spo15}$ or $P_{veg}$. The introduction of such a strong promoter results in an increase in riboflavin production which is at least 50%, 75%, 100%, 200%, 250%, 300%, 350%, 500% or even more than 1000% compared to a microorganism carrying a modified rib leader downstream of the natural promoter. This may be furthermore increased by overexpression of one or more rib gene(s), in particular ribA or by introduction of multiple copies of the rib operon in the host cell, such as implemented in *B. subtilis* strain RB50 (see e.g. EP 405370). Compared to the riboflavin production in *B. subtilis* RB50, the riboflavin production can be increased by at least 100%, 200%, 250%, 500%, or even more than 750% by genetically altering a microorganism such that it carries a modification in the rib leader as defined herein fused to a strong promoter. A microorganism carrying a modified rib leader as defined herein optionally combined with the introduction of a strong promoter and/or multiple copy/copies of the rib operon may be furthermore altered via a decoupling of growth from production of riboflavin, such as e.g. via introduction of an auxotrophy such as described in EP 1186664 for e.g. biotin, and/or furthermore combined with introduction of modified transketolase gene as e.g. described in WO 07/051,552.

The present invention provides a modified rib leader as defined herein carrying (i) one or more ribO mutations together with modifications at the 3' end of the rib leader or (ii) deletions of the terminator and 5' flanking regions thereof, wherein said modified rib leaders are fused to strong promoters, such as e.g. $P_{spo15}$ or $P_{veg}$.

A particular preferred strain for the production of riboflavin is *B. subtilis*. A more preferred strain is *B. subtilis* RB50::[pRF69]$_n$ containing multiple (n) copies (for example about 5 to about 20 copies) of pRF69 encoding a rib operon modified with the strong promoter $P_{spo15}$ to enhance transcription of the rib genes (see e.g. EP 405370 and Perkins et al., J. Ind. Microbiol. Biotechnol., 22:8-18, 1999 for construction of the strain and culture conditions to result in riboflavin production). *B. subtilis* RB50 and plasmid pRF69 may be available from NRRL (accession number B 18502) and ATCC (accession number ATCC 68338), respectively.

In accordance with a further object of the present invention there is provided the use of a modified polynucleotide as defined above or a microorganism which is genetically engineered with such polynucleotides for the riboflavin production.

The invention also relates to processes for the expression of a (modified) rib operon including a modified rib leader in a microorganism, to processes for the production of (modified) polynucleotides as defined above in a microorganism and to processes for the production of such modified microorganisms capable of producing riboflavin. All these processes may comprise the step of altering a microorganism, wherein "altering" as used herein encompasses the process of "genetically altering" in such a way that both the yield and/or productivity of riboflavin and the accumulation of intact, full-length rib mRNA can be improved compared to the wild-type microorganism. The term "altering" also includes the generation of modified polynucleotides as described herein, in particular modification of the rib leader. As used herein, "improved yield of riboflavin" means an increase of at least 50%, 75%, 100%, 200%, 250%, 300%, 350%, 500% or even more than 10000% or 100000% (see above), compared to a wild-type/non-modified microorganism, i.e. a microorganism which is not genetically altered.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, addition, insertion, deletion, transfection, transformation using plasmids, viruses, or other vectors. A genetically modified organism, e.g. genetically modified microorganism, is also often referred to as a recombinant organism, e.g. recombinant microorganism. A genetically engineered microorganism carries a modified rib leader as defined above.

According to the invention a genetically engineered/recombinantly produced host cell (also referred to as recombinant cell or transformed cell) is provided carrying such modified rib leader as of the present invention such that the yield, production and/or efficiency of production of riboflavin is improved. The host cell may be selected from a microorganism capable of producing riboflavin from a given carbon source, in particular *Bacillus*, preferably *B. subtilis*.

A "transformed cell" or "recombinant cell" is a cell into which (or into an ancestor of which) has been introduced, by means of recombinant DNA techniques, a nucleic acid according to the invention leading to increased and/or enhanced accumulation of intact, full-length rib mRNA. It also includes introduction of one or more mutations into a wild-type rib leader already present in said cell. Suitable host cells include cells of microorganisms capable of producing riboflavin, e.g., converting a given carbon source into riboflavin as defined above. Useful strains for performing said fermentation process are listed above and are known in the art.

The nucleic acids of the present invention are preferably provided in an isolated form, and preferably purified to homogeneity.

The term "isolated" means that the material is removed from its original environment (e.g., the natural environment if it is naturally occurring). For example, a naturally-occurring polynucleotide present in a living microorganism is not isolated, but the same polynucleotide, separated from some or all of the coexisting materials in the natural system, is isolated. Such polynucleotides could be part of a vector and/or such polynucleotides could be part of a composition and still be isolated in that such vector or composition is not part of its natural environment.

As used herein, the term "gene" refers to nucleic acid molecules which may be isolated from chromosomal DNA, which include an open reading frame encoding a protein, e.g. proteins involved in the synthesis of riboflavin, such as for instance enzymes from the *B. subtilis* riboflavin biosynthetic pathway.

A gene may include coding sequences, non-coding sequences such as for instance untranslated sequences located at the 3' and 5' ends of the coding region of a gene, such as for instance promoter regions, regulator regions and terminator regions important for the appropriate expression and stabilization of the polypeptide derived thereof.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

Unless otherwise indicated, all nucleotide sequences determined by sequencing a DNA molecule herein were determined using an automated DNA sequencer. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art.

The person skilled in the art is capable of identifying such erroneously identified bases and knows how to correct for such errors.

Polynucleotides according to the invention irrespective of whether they are modified or non-modified may be used as hybridization probes or PCR primers. Included is furthermore the use of polynucleotides as described herein for enhancing and/or improving the function or activity of homologous rib leader sequences in other organisms which are closely related to *Bacillus* and as described above as suitable host cells. As used herein, the term "homologous rib leader sequences" encompasses rib leader sequences from different organisms according to FIG. 2 in Vitreschak et al., Nucleic Acid Res 30, 3141-3151, 2002, wherein different RFN elements have been aligned. With this alignment the skilled person can easily identify parts of the rib leader corresponding to the ones described herein originating from *B. subtilis* in order to generate modified rib leader sequences in the listed organisms as described herein.

The invention also relates to an isolated polynucleotide hybridizable under stringent conditions, preferably under highly stringent conditions, to a polynucleotide as of the present invention, such as for instance a polynucleotide shown in SEQ ID NOs:42, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, preferably selected from SEQ ID NO: 42, 67, 68, 69, 71, 70. Advantageously, such polynucleotide may be obtained from a microorganism capable of producing riboflavin, in particular *Bacillus subtilis*.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

A preferred, non-limiting example of stringent hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include incubations at 42° C. for a period of several days, such as 2-4 days, using a labeled DNA probe, such as a digoxygenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Furthermore, oligonucleotides corresponding to or hybridizable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two nucleic acid sequences, the sequences are aligned for optimal comparison purposes (e.g., gaps may be introduced in the sequence of a first nucleic acid sequence for optimal alignment with a second nucleic acid sequence). The nucleotides at corresponding positions are then compared. When a position in the first sequence is occupied by the same nucleotide as the corresponding position in the second sequence, then the molecules are identical at that position. The percent identity between the two sequences is a function of the number of identical positions shared by the sequences [i.e., % identity=number of identical positions/total number of positions (i.e., overlapping positions)×100]. Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. 48, 444-453, 1970) algorithm which has been incorporated into the GAP program in the GCG software package (available at http://www.accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.accelrys.com), using a NWSgapdna.CMP matrix and a gap weight of 40, 50, 60, 70 or 80 and a length weight of 1, 2, 3, 4, 5 or 6. In another embodiment, the percent identity between two nucleotide sequences is determined using the algorithm of E. Meyers and W. Miller (CABIOS, 4: 11-17, 1989) which has been incorporated into the ALIGN program (version 2.0) (available at http://vega.igh.cnrs.fr/bin/align-guess.cgi) using a PAM120 weight residue table, a gap length penalty of 12 and a gap penalty of 4.

A useful method for constructing a microorganism as of the present invention, i.e. introducing a modified rib leader in the 5' untranslated region of a gene involved in production of riboflavin is given in the examples, wherein introduction of a herein disclosed modified rib leader leads to a more intact, full-length mRNA transcripts from the respective rib gene(s) which furthermore leads to increased yield and/or productivity of riboflavin. Selection of recombinant microorganisms can be performed via introduction of an antibiotic resistance gene, such as for instance chloramphenicol, neomycin, streptomycin, spectinomycin or the like.

The present invention is directed to fermentative production of riboflavin using a microorganism carrying a modified rib leader. As used herein, the term "riboflavin" includes but is not limited to riboflavin, flavin mononucleotide (FMN), flavin adenine dinucleotide (FAD), as well as precursors, derivatives and salts of riboflavin, FMN or FAD, such as e.g. riboflavin-5-phosphate or sodium riboflavin-5-phosphate. Precursors and/or derivatives of riboflavin, FMN and FAD may be selected from e.g. DRAPP; 5-amino-6-ribosylamino-2,4 (1H,3H)-pyrimidinedione-5'-phosphate; 2,5-diamino-6-ribitylamino-4 (3H)-pyrimidinone-5'-phosphate; 5-amino-6-ribitylamino-2,4 (1H,3H)-pyrimidinedione-5'-phosphate; 5-amino-6-ribitylamino-2,4 (1H,3H)-pyrimidinedione; 6,7-dimethyl-8-ribityllumazine (DMRL); and flavoproteins. The terms "riboflavin" and "vitamin B2" are used interchangeably herein. The genes involved in biosynthesis of riboflavin as well as methods for fermentative production of riboflavin, in particular fermentative production using *Bacillus* strains, are known (see e.g. EP 405370 or Ullman's Encyclopedia of Industrial Chemistry, 7th Edition, 2007, Chapter Vitamins). These methods may be also applied for production of riboflavin using mutant strains comprising modified rib leader sequences as described herein.

Several substrates may be used as a carbon source in a process of the present invention, i.e. a process for production of riboflavin as mentioned above. Particularly suited carbon sources may be selected from compounds consisting of 3, 5 or 6 carbon atoms, such as e.g. D-glucose, glycerol, thick juice, dextrose, starch, sucrose or ribose. Preferably, the carbon source is D-glucose. The term "carbon source", "substrate" and "production substrate" in connection with the above process is used interchangeably herein.

A medium as used herein for the above process using a modified microorganism may be any suitable medium for the production of riboflavin. Typically, the medium is an aqueous medium comprising for instance salts, substrate(s), and a certain pH. The medium in which the substrate is converted into riboflavin is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into riboflavin.

The produced riboflavin may be recovered from the cells by any suitable means. Recovering means for instance that the produced riboflavin may be separated from the production medium. Optionally, the thus produced fermentation product may be further processed, e.g. purified.

In connection with the above process using a microorganism, in one aspect, the growing step can be performed in an aqueous medium, i.e. the growth medium, supplemented with appropriate nutrients for growth normally under aerobic conditions. The cultivation may be conducted, for instance, in batch, fed-batch, semi-continuous or continuous mode, wherein fed-batch or semi-continuous mode is preferred.

The cultivation period may vary depending on for instance the host, pH, temperature and nutrient medium to be used, and may be for instance about 10 h to about 10 days, preferably about 4 to about 7 days, more preferably about 2 to about 6 days, depending on the microorganism. The skilled person will know the optimal culture conditions of suitable microorganisms.

The cultivation may be conducted for instance at a pH of about 7.0, preferably in the range of about 6 to about 8, more preferably about 6.5 to 7.5. A suitable temperature range for carrying out the cultivation may be for instance from about 13° C. to about 70° C., preferably from about 35° C. to about 39° C., more preferably from about 30° C. to about 39° C., and most preferably from about 36° C. to about 39° C. The culture medium for growth usually may contain such nutrients as assailable carbon sources, e.g., D-glucose, glycerol, thick juice, dextrose, starch, sucrose or ribose; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as described above in such a way that they convert these substrates into the desired target fermentation product. Incubation can be conducted in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing the desired fermentation product. Alternatively, incubation can be conducted in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride. An example of a suitable medium for production of riboflavin is described in WO 04/113510 (VF-medium), which is particularly useful with regards to *Bacillus*.

The terms "production" or "productivity" are art-recognized and include the concentration of riboflavin formed within a given time and a given fermentation volume (e.g., kg product per hour per liter). The term "efficiency of production" includes the time required for a particular level of production to be achieved (for example, how long it takes for the cell to attain a particular rate of output of a fermentation product). The term "yield" is art-recognized and includes the efficiency of the conversion of the carbon source into the product (i.e., riboflavin). This is generally written as, for example, kg product per kg carbon source. By "increasing the yield and/or production/productivity" of the compound it is meant that the quantity of recovered molecules, or of useful recovered molecules of that compound in a given amount of culture over a given amount of time is increased.

Analytical methods for determining the yield/productivity of riboflavin are known in the art. Such methods may include, but are not limited to HPLC or use of indicator strains (see e.g. Bretzel et al., J. Ind. Microbiol. Biotechnol. 22, 19-26, 1999).

BRIEF DESCRIPTION OF THE DRAWINGS

FIG. 1 shows the rib leader of *Bacillus subtilis* including 5' and 3' flanking regions thereof. The rib leader is located between nucleotide positions 562 to 857. (A) wild-type rib operon wherein 5' regulatory elements are indicated in bold ("ttgcgt" and "tataat", respectively) as well as the transcription start ("A") corresponding to the first nucleotide of the rib leader as shown in SEQ ID NO:42. (B) rib leader wherein the positions of ribO mutations such as triple ribO, RK41 and RK1a are indicated in bold. (C) to (I) rib leader wherein the position of flank-right, terminator, stem loop-right, stem loop-left, SWITCH deletion, del mro175, and the entire rib leader, respectively, is indicated through underlining. For more explanation see text, in particular the examples. FIGS. 1A-B disclose SEQ ID NOS 93-94, respectively and FIGS. 1C-I each disclose SEQ ID NO: 93.

Figure 2:
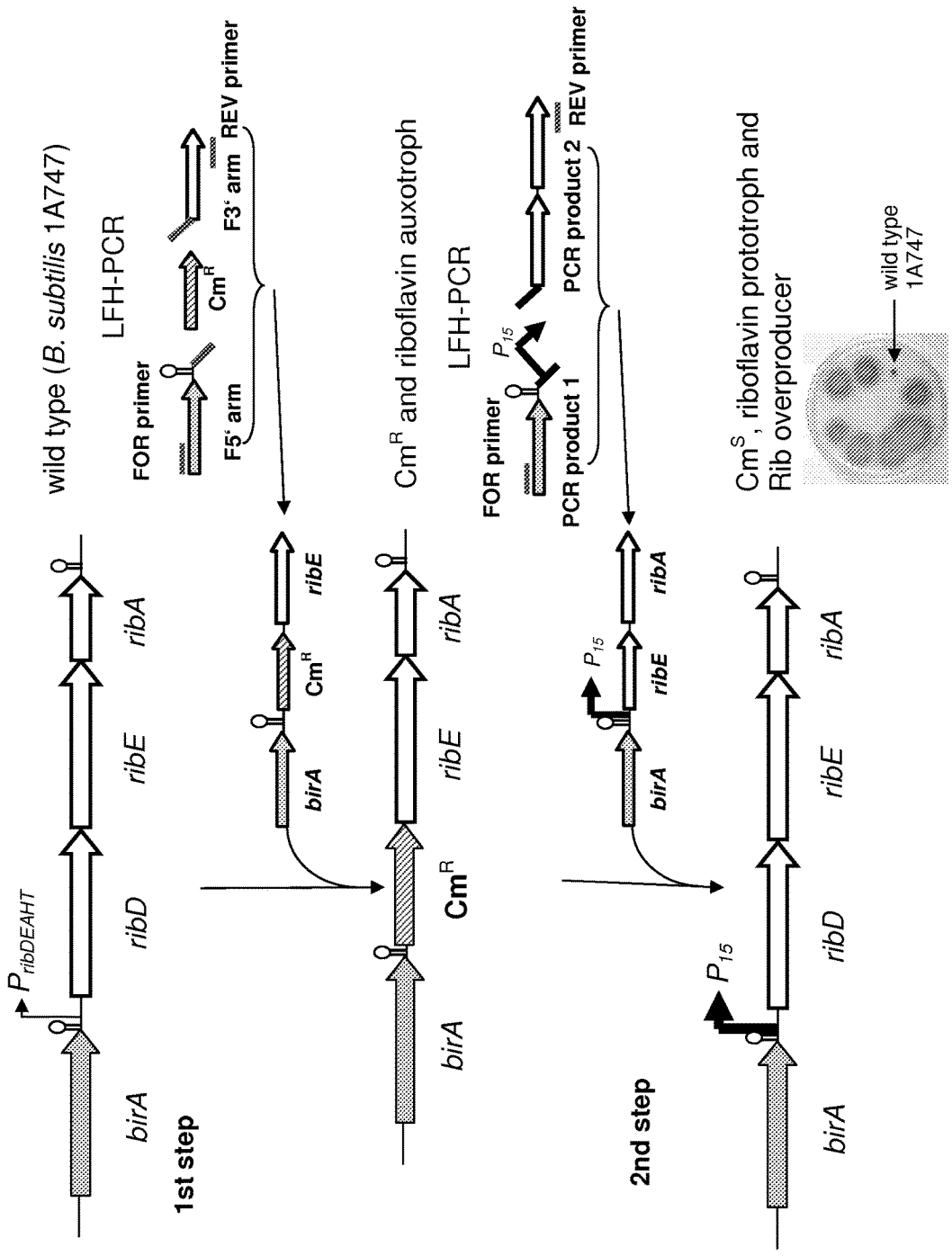
FIG. 2 shows the different steps for constructing a genetically altered microorganism carrying an mRNA stabilizing element (St) downstream of a strong constitutive $P_{spo15}$ promoter via LFH-PCR which is located at the 5' end of the rib operon comprising the genes ribD, ribE, ribA. For selection of recombinant microorganisms, the chloramphenicol (Cm) antibiotic resistance cassette is used. (A) Replacement of the native promoter with a strong promoter using LFH-PCR. (B) Introduction of mRNA stabilizing elements. For more explanation see the examples.
Figure 2:
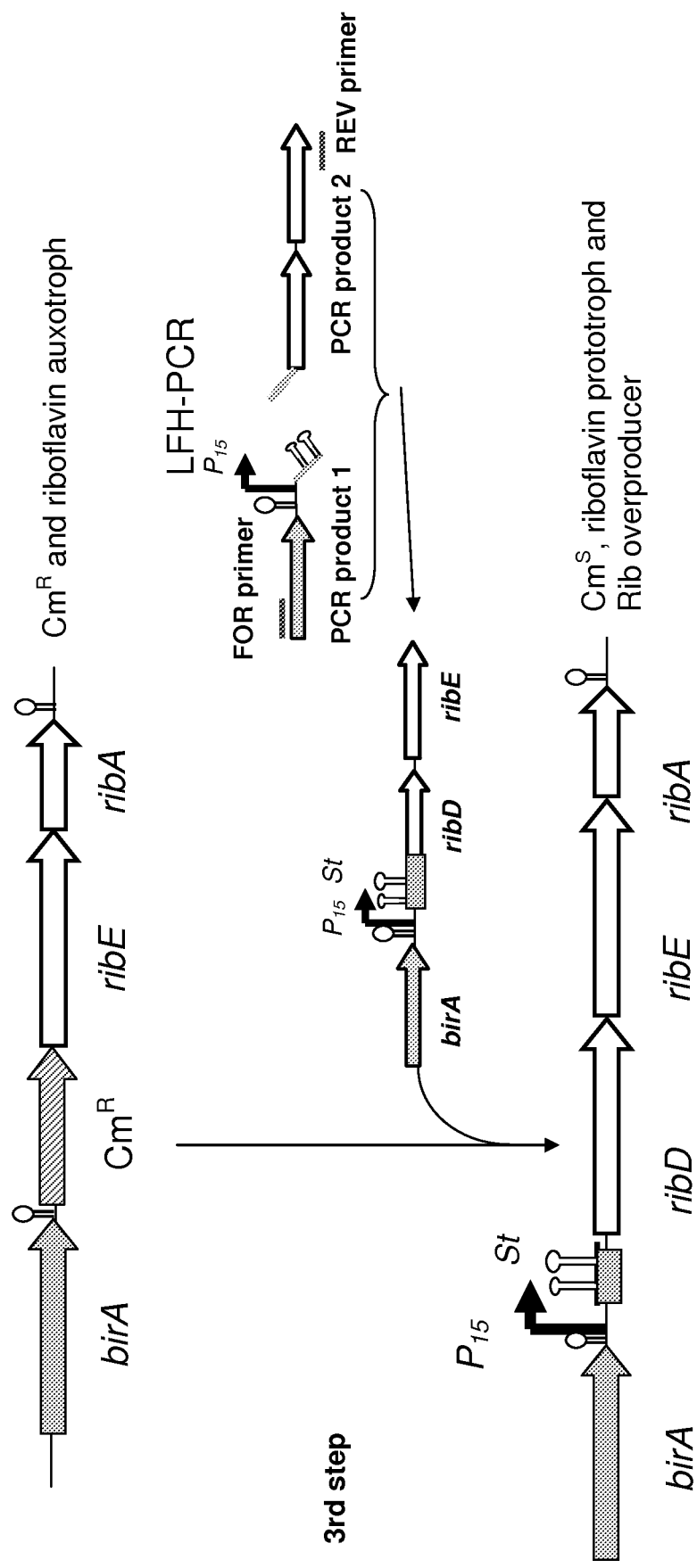

The following examples are illustrative only and are not intended to limit the scope of the invention in any way. The contents of all references, patent applications, patents and published patent applications, cited throughout this application are hereby incorporated by reference, in particular EP 405370, WO 04/106557, WO 07/051,552 and EP1186664.

EXAMPLES

The following media as referred to in the examples are described in WO 04/106557: Tryptose Blood Agar Broth (TBAB) medium, Veal infusion-Yeast Extract broth (VY) medium, 10× Spizizen salts and Minimal Medium (MM). Additionally, the following media have been used:

100× Trace elements solution A: 12.5 g $MgCl_2.6H_2O$; 0.55 g $CaCl_2$; 1.35 g $FeCl_2.6H_2O$; 0.1 g $MnCl_2.4H_2O$; 0.17 g/l $ZnCl_2$; 0.043 g $CuCl_2.2H_2O$; 0.06 g $CoCl_2.6H_2O$; 0.06 g $Na_2MoO_4.2H_2O$; ad $11H_2O$, autoclaved.

5× Minimal Salt Solution: 0.057 M $K_2SO_4$; 0.31 M $K_2HPO_4.5H_2O$; 0.22 M $KH_2PO4$; 0.017 M Na-citrate.$7H_2O$; 0.004 M $MgSO_4.H_2O$, pH 7.0, autoclaved.

100× Trace elements solution B: 0.55 g $CaCl_2$; 0.17 g $ZnCl_2$; 0.043 g $CuCl_2.2H_2O$; 0.06 $CoCl_2.6H_2O$; 0.06 g $Na_2MoO_4.2H_2O$; ad $11H_2O$, autoclaved.

Riboflavin screening medium (RSM): 200 ml 10× Spizizen salts; 10 ml 100× Trace elements solution A; 2 ml 50% glucose; 36 ml 25% raffinose; 10 ml 10% yeast extract; ad $11H_2O$.

Spizizen Minimal Medium (SMM): 100 ml 10× Spizizen salts; 10 ml 50% glucose; 1 ml 40% sodium glutamate; 10 ml trace element solution A; ad $11H_2O$.

Riboflavin production in shake flasks were performed as follows: strains were inoculated from frozen glycerol stocks in 5 ml VY rich medium and grown overnight at 37° C. with an agitation of 280 rpm. Cells were collected by centrifugation and resuspended in 1 ml RSM (see above). 250 µl of the cell suspension was used for inoculation of 25 ml RSM in 250 ml baffled shake flasks. After 48 h incubation at 39° C. with an agitation of 220 rpm, 500 µl culture were taken and 35 µl 4 N NaOH were mixed with the sample for 1 min at room temperature allowing to dissolve the riboflavin crystals. Samples were neutralized by the addition of 465 µl 1 M potassium phosphate buffer (pH 6.8) and pelleted by centrifugation (5 min, 13200 rpm). The supernatant was used for HPLC determination of the concentrations of riboflavin and two side products: 6,7-dimethyl-8-ribityllumazine (DMRL) and oxolumazine. In addition, a second culture sample was taken and after centrifugation (5 min, 13200 rpm) the supernatant was used for the determination of the concentrations of the residual glucose and raffinose in the medium for calculation of the riboflavin yield on carbon source.

Samples from shake flask cultures were analyzed by HPLC. Chromatography was carried out on an Agilent 1100 HPLC system equipped with a thermostatted autosampler, a diode array and a fluorescence detector. The separation was performed on a Supelcosil LC-8 DB-5µ column (150 mm×4.6 mm) equipped with a 4 mm LC-8 DB guard column. A mixture of 0.1 M acetic acid and methanol was used as mobile phase. Gradient elution was applied starting at 2% methanol (constant for 5 min) and going up to 50% methanol in 15 min. The column was kept at 20° C. The signal was recorded by UV at 280 nm. Riboflavin was well separated from the impurities (e.g. side products: DMRL and oxolumazine) and eluted at 15.2 min. The calibration is based on reference material obtained from Fluka. The method is calibrated from 10 µg/ml to 1 mg/ml riboflavin.

Additionally, the concentration of glucose and raffinose in the culture broth was analyzed by an Agilent 1100 series HPLC system using a quaternary pump, an autosampler a UV—and a refractive index detector. The separation was achieved on a CAPCELL PAK NH2 UG80 column (4.6 mm×250 mm, 5µ) (Shiseido). The optimal column temperature was 35° C. The mobile phase was a mixture of acetonitrile and DI water at a 65/35 ratio. The flow rate was 1.0 ml/min and the injection volume set to 5 µl. The refractive index signal was monitored and used for detection. The calibration range for each compound is from 0.5 mg/ml to 30 mg/ml.

Example 1

Generation of Riboflavin Auxotrophic Strains

For engineering of the original leader and promoter sequence of the riboflavin operon of B. subtilis, the riboflavin promoter, the 5' leader sequence and the 5' part of ribD (ribG) coding for the deaminase domain of RibD was replaced by a neomycin resistance (neo) cassette obtained from plasmid pUB110 (Itaya et al., 1989, Nucleic Acid Res. 17:4410) generating the riboflavin-auxotrophic strain B. subtilis BS3813. Genomic DNA derived from B. subtilis strain 1A747 (SPβ$^c$, prototroph), which is a derivative of B. subtilis 168 (trpC2), has been obtained from the Bacillus Genetic Stock Center, The Ohio State University, Columbus, Ohio 43210 USA.

For strain construction, Long Flanking Homology Polymerase Chain Reaction (LFH-PCR) was used to generate DNA fragments containing the 1236 bp neo resistance cassette flanked with the 526 bp upstream region of the native $P_{rib}$ promoter (flank 5') and the 502 bp 3' end of ribD gene (flank 3'). Therefore, 3 DNA fragments flank 5', the neo resistance cassette and flank 3' were first amplified by PCR. DNA fragments flank 5' and flank 3' were generated as follows: 1 µl of a 100 µM solution of primers p50 (SEQ ID NO:6) together with p51 (SEQ ID NO:7) or primers p44 (SEQ ID NO:4) together with p45 (SEQ ID NO:5) were added to 0.1 µg B. subtilis 1A747 chromosomal DNA in a 50 µl reaction volume containing 1 µl of 10 mM dNTP's, 5 µl of 10× buffer and 0.5 µl Pfu polymerase (Stratagene). For generating DNA fragment containing the neo resistance cassette, 1 µl of a 100 µM solution of primers p9 (SEQ ID NO:2) together with p10 (SEQ ID NO:3) were added to 0.05 µg pUB 110 DNA containing the neo resistance cassette in a 50 µl reaction volume containing 1 µl of 10 mM dNTP's, 5 µl of 10× buffer and 0.5 µl Pfu polymerase (Stratagene). The PCR reactions were performed in 35 cycles of three sequential steps: (i) denaturing step at 94° C. for 30 sec; (ii) annealing step at 52° C. for 30 sec; (iii) elongation step at 72° C. for 1 min. The PCR cycles were preceded by a denaturation step at 95° C. for 3 min. The three PCR products were separated by agarose gel electrophoresis and extracted from the gel using the MinElute Gel Extraction Kit (Qiagen). In the final LFH-PCR reaction, the three purified PCR products (flank 5', neo resistance cassette and flank 3') were assembled: 1 µl of a 100 µM solution of primers p45 together with p51, 1 µl flank 5' PCR product (50 ng), 1 µl flank 3' PCR product (50 ng) and 1 µl neo resistance cassette (100 ng) were added to give a final reaction volume of 50 µl containing 1 µl of 10 mM dNTP's, 5 µl of 10× buffer and 0.5 µl Pfu polymerase (Stratagene). The LFH-PCR reaction was performed in 35 cycles of three sequential steps: (i) denaturing step at 94° C. for 30 sec; (ii) annealing step at 52° C. for 30 sec; (iii) elongation step at 72° C. for 2.5 min. The PCR cycles were preceded by a denaturation step at 95° C. for 3 min. The assembled LFH-PCR product was purified by using the QiaQuick PCR purification kit (Qiagen). The purified LFH-PCR product (2 µg) was used for transformation of competent B. subtilis 1A747 cells. Neomycin-resistant (Nm$^r$) transformants were selected on TBAB plates containing 2 mg/l neomycin and 100 mg/l riboflavin. The correct genotype of the resulting riboflavin-auxotrophic and Nm$^r$ BS3813 strain was confirmed by two PCR reactions using primers p45 together with p10, and primers p51 together with p9, and chromosomal DNA of the transformants as template DNA. The PCR reactions were performed using standard reaction conditions as described above for the generation of DNA fragments flank 5' and flank 3'. In addition, the sequence of ribD from BS3813 was confirmed by sequencing.

Transduction of the deletion construct was performed with PBS-1 phage according to the method described in WO 07/051,552 (see Example 6), wherein a lysate of BS3813 was used for transducing the riboflavin-overproducing strain B. subtilis BS3534 carrying a mutation in the transketolase gene (for construction of BS3534 see WO 07/051,552). BS3534 is based on the riboflavin-overproducing strain B. subtilis RB50, which is described in detail in EP 405370 and available under the deposition number NRRL B-18502. $Nm^r$ transductants were selected on TBAB agar plates containing 2 mg/l neomycin and 100 mg/l riboflavin. The genotype of isolated transductants was confirmed by PCR as described above. The resulting strain was designated BS3798.

Example 2

Generation of Strains Carrying Modified Rib Leader Sequences

Two types of mutations were introduced into the rib leader to deregulate the transcription of the rib genes wherein type I refers to ribO mutations and type II refers to (partial) deletions of the rib leader (see FIG. 1).

Three ribO mutations were generated, i.e. C85T named "RK41", G121A named "RK1a" and a triple combination G39A-G40A-G41A named "triple ribO". For the type II mutants, the following parts were deleted from the rib leader, wherein the numbering of nucleotides refers to the rib leader sequence shown in SEQ ID NO:42 isolated from B. subtilis: deletion of nucleotides 250 to 257 (SEQ ID NO:36) named "del stem loop-right", deletion of nucleotides 231 to 238 (SEQ ID NO:37) named "del stem loop-left", deletion of nucleotides 239 to 263 (SEQ ID NO:38) named "del flank-right", deletion of nucleotides 231 to 263 (SEQ ID NO:39) named "del terminator", deletion of nucleotides 166 to 263 (SEQ ID NO:40) named "SWITCH deletion", deletion of nucleotides 135 to 263 (SEQ ID NO:41) named "del mro175" and a deletion of the complete leader, i.e. nucleotides 1 to 263 (SEQ ID NO:42) named "leader deletion". In the case of the mro175 deletion, also an insertion of four nucleotides took place (5'-ATGG-3').

Construction of strains carrying modified rib leader sequences together with the rib promoter (SEQ ID NOs:45-54) were basically performed via two PCR reactions according to the protocol/conditions outlined in Example 1 wherein in a first PCR reaction, the two DNA fragments designated flank 5' and flank 3' were generated using chromosomal DNA from B. subtilis 1A747. In a second PCR reaction according to the protocol/conditions as described in Example 1, these two PCR-fragments were assembled using primers p45 and p51. The respective primer-pairs for the first PCR reactions, i.e. primers for generation of flank 5' and primers for generation of flank 3' resulting in the desired mutations/deletions (see above) are listed in Table 1, column 2 and 3, respectively. After purification using the QiaQuick PCR purification kit (Qiagen), 2 µg of the purified full-length PCR product was used for transformation of competent B. subtilis BS3813 cells (see Example 1). The cells were plated onto SMM plates. Riboflavin-prototroph transformants were suspended in 1 ml 0.9% NaCl solution. 100 µl of a 500-fold dilution of the original cell suspension was plated onto TBAB agar plates. Single colonies were transferred onto fresh TBAB agar plates and onto TBAB agar plates supplemented with 2 mg/l Nm and 100 mg/l riboflavin. Correct transformants were sensitive to neomycin and thus grew only on TBAB agar plates and did not grow on plates supplemented with neomycin. In addition, the genotype was confirmed by sequencing of the newly introduced rib promoter and ribD. The newly generated B. subtilis strains containing the respective mutations/deletions in the rib leader were designated as shown in Table 1, column 4.

PBS-1 lysates from the newly generated strains were prepared and used for transduction of BS3798 (generated in Example 1). Transduced cells were selected on SMM plates. The riboflavin-prototrophic B. subtilis transductants suspended in 1 ml 0.9% NaCl solution. 100 µl of a 500-fold dilution of the original cell suspension was plated onto TBAB agar plates. Single colonies were transferred onto fresh TBAB agar plates and TBAB agar plates supplemented with 2 mg/l Nm and 100 mg/l riboflavin. Correct transductants grew only on TBAB agar plates and were therefore neomycin-sensitive. The newly transduced strains were named as indicated in Table 1, column 5.

TABLE 1

Primer pairs used for construction of flank 5' and flank 3' fragments, respectively, resulting in modified rib leader sequences and the designation of the resulting strains either transformed with said PCR-fragments or transduced with the respective lysates (for more explanation see text).

| Designation of rib leader mutation | Flank 3' primer pair (SEQ ID NOs) | Flank 5' primer pair (SEQ ID NOs) | Transformed strains | Transduced strains |
|---|---|---|---|---|
| RK1a | p74/p51 (20/7) | p45/p75 (5/21) | BS3833 | BS3839 |
| RK41 | p72/p51 (16/7) | p45/p73 (5/18) | BS3958 | BS3987, BS3988, BS3989 |
| triple ribO | p72a/p51 (17/7) | p45/p73a (5/19) | BStriple_ribO | |
| del flank-right | p56/p51 (8/7) | p45/p57 (5/9) | BS3814 | BS3832 |
| del terminator | p58/p51 (10/7) | p45/p59 (5/11) | BS3815 | BS3821 |
| del stem loop-right | p76/p51 (22/7) | p45/p77 (5/23) | BS3842 | BS3846 |
| del stem loop-left | p79/p51 (25/7) | p45/p78 (5/24) | BS3847 | BS3859 |
| SWITCH deletion | p80/p51 (26/7) | p45/p81 (5/28) | BS3867 | BS3900, BS3916 |
| del mro175 | p80a/p51 (27/7) | p45/p81a (5/29) | BSmro175 | |
| Leader deletion | p96/p51 (31/7) | p45/p95 (5/30) | BSleader | |

Transformed strains: designation of B. subtilis strains after transformation of B. subtilis BS3813 (neo-resistant; B2-auxotroph based on the wt-strain B. subtilis 1A747) with the respective PCR-fragment; Transduced strains: designation of B. subtilis strains after transduction of B. subtilis BS3798 (neo-resistant, B2-auxotroph based on B. subtilis RB50) with lysate of the respective strains according to column 4. For more explanation see text.

The newly generated strains were tested for riboflavin production in shake flask screening as described above. After 48 h, the riboflavin of a 500 µl sample was dissolved by addition of 4 N NaOH, neutralized and after centrifugation, the riboflavin concentration of the processed sample was determined by HPLC together with the concentration of DMRL and oxolumazine, a degradation product of DMRL. For calculation of the riboflavin yield on carbon source, the starting and residual concentration of all carbon sources were determined by HPLC.

The results are presented in Table 2. While the native rib operon in a wild-type strain (1A747) background basically does not secrete any riboflavin into the medium, the same rib operon in a strain background selected for riboflavin overproduction (RB50) secreted a measurable amount of riboflavin. The best results were obtained with the ribO mutant RK41 in both the wt (BS3958) and the RB50 background (BS3987), respectively. Deletion of the terminator did not result in the expected results, in particular in the wt background (BS3815). While in the wt background the second best results were obtained with RK1a ribO mutants (BS3833), the second best results in the RB50 background were achieved with the SWITCH deletion (BS3900 and BS3916), which showed even a higher yield in riboflavin than the leader deletion strain.

TABLE 2A

Riboflavin production with transformed *B. subtilis* strains as indicated based on the wt strain *B. subtilis* 1A747 carrying the native rib leader. The yield is given as g riboflavin per g carbon source (for more explanation see text).

| Strain | Rib leader mutation | Yield [%] |
|---|---|---|
| 1A747 | wild-type | 0.0004 |
| BS3833 | RK1a | 0.0570 |
| BS3958 | RK41 | 0.1100 |
| BS3814 | del flank-right | 0.0090 |
| BS3815 | del terminator | 0.0103 |
| BS3867 | SWITCH deletion | 0.0139 |

TABLE 2B

Riboflavin production with transduced *B. subtilis* strains as indicated based on the riboflavin-overproducing strain *B. subtilis* RB50 carrying the native rib leader. The yield is given as g riboflavin per g carbon source (for more explanation see text).

| Strain | Rib leader mutation | Yield [%] |
|---|---|---|
| RB50 | wild-type rib operon | 0.46 |
| BS3839 | RK1a | 1.29 |
| BS3987 | RK41 | 1.64 |
| BS3832 | del flank-right | 0.33 |
| BS3821 | del terminator | 0.74 |
| BS3900, BS3916 | SWITCH deletion | 1.48 |
| BS3846 | del stem loop-right | 0.11 |
| BS3859 | del stem loop-left | 0.52 |

Example 3

Replacing the Native Rib Promoter by Strong Constitutive Promoters

In order to evaluate a possible synergistic effect of rib leader mutations combined with a strong promoter, the original rib promoter of the newly generated constructs (see Example 2) was replaced either by the strong constitutive promoter $P_{veg}$ or by $P_{Spo15}$. The way of construction closely resembled the approach of Example 2. For generation of the DNA fragments flank 3' and flank 5', 1 µl of a 100 µl solution of primer p60 (SEQ ID NO:12) together with p51 (for construction of $P_{veg}$) or primer p62 (SEQ ID NO:14) together with p51 (for construction of $P_{Spo15}$) and primer pair p45 together with p61 (SEQ ID NO:13) (for construction of $P_{veg}$) or primer p45 together with p63 (SEQ ID NO:15) (for construction of $P_{Spo15}$) were added to 0.1 µg 1A747 chromosomal DNA in a 50 µl reaction volume containing 1 µl of 10 mM dNTP's, 5 µl of 10× buffer and 0.5 µl Pfu polymerase (Stratagene). The PCR reactions were performed for 35 cycles of three sequential steps: (i) denaturing step at 94° C. for 30 sec; (ii) annealing step at 52° C. for 30 sec; (iii) elongation step at 72° C. for 1 min. The cycles were preceded by a DNA denaturation step at 95° C. for 3 min. The two PCR products were separated by agarose gel electrophoresis and extracted from the gel using the MinElute Gel Extraction Kit (Qiagen). In the final PCR reaction, the two purified PCR products (flank 5' and flank 3') were assembled: 1 µl of a 100 µM solution of primers p45 and p51, 1.0 µl flank 5' PCR product (50 ng) and 1.0 µl flank 3' PCR product (50 ng) were mixed in a 50 µl final reaction volume containing 1 µl of 10 mM dNTP's, 5 µl of 10× buffer and 0.5 µl Pfu polymerase (Stratagene). The PCR reaction was performed for 35 cycles of three sequential steps: (i) denaturing step at 94° C. for 30 sec; (ii) annealing step at 52° C. for 30 sec; (iii) elongation step at 72° C. for 2.5 min. The PCR cycles were preceded by a denaturation step at 95° C. for 3 min. The assembled PCR product was purified by using the QiaQuick PCR purification kit (Qiagen). The purified full-length PCR product (2 µg) was used for transformation of competent *B. subtilis* BS3813 cells. The cells were plated onto SMM plates. Riboflavin-prototrophic *Bacillus* transformants were suspended in 1 ml 0.9% NaCl solution. 100 µl of the 500-fold dilution of the original cell suspension was plated on TBAB agar plate. Single colonies were transferred onto fresh TBAB agar plates and onto TBAB agar plates supplemented with 2 mg/l Nm and 100 mg/l riboflavin. Correct transformants grew only on TBAB agar plates and therefore were neomycin-sensitive. In addition, the genotype was confirmed by sequencing of the newly integrated promoter, rib leader and ribD. The strain with a $P_{veg}$ driven rib operon was called BS3811, the strain with the $P_{Spo15}$ driven rib operon was called BS3817.

In order to combine the strong promoters with the leader modifications, the gDNA of strain 1A747 was replaced by gDNA of strain BS3811 ($P_{veg}$ promoter) and BS3817 ($P_{Spo15}$ promoter), respectively, in all described PCR reactions of Example 2. All other conditions of each PCR reaction including the used primer pairs were kept identical. The final PCR products were transformed into BS3813 and obtained transformants were verified as described (Example 2). In the case of the construct $P_{Spo15}$_leader deletion, the primer pairs p45/p95 for the flank 5' PCR product and p96/p51 for the flank 3' PCR product were used as indicated in Table 4. All other steps were performed as described above. The following constructs were made, with the designation of the resulting *B. subtilis* strain transformed with said constructs in brackets: $P_{veg}$_del flank-right (BS3840), $P_{SPo15}$_del flank-right (BS3831), $P_{veg}$_del terminator (BS3844), $P_{Spo15}$_del terminator (BS3871), $P_{Spo15}$_SWITCH deletion (BS3874), $P_{Spo15}$_leader deletion (BS3944), $P_{veg}$_RK41 (BS3887), $P_{veg}$_RK1a (BS3953), $P_{Spo15}$_RK1a (BS3884), $P_{veg}$_triple ribO (BS3912).

PBS-1 lysates were prepared from the strains mentioned above and transduced into BS3798. Transduced cells were selected on SMM plates. The riboflavin-prototrophic *B. subtilis* transformants were suspended in 1 ml 0.9% NaCl solution. 100 µl of the 500-fold dilution of the original cell suspension was plated onto TBAB agar plates. Single colonies were transferred onto fresh TBAB agar plates and TBAB agar plates supplemented with 2 mg/l Nm and 100 mg/l riboflavin. Correct transformants grew only on TBAB agar plates and were therefore neomycin-sensitive. The following strains were generated: BS3970 and BS3971 transduced with PBS-1 lysate from BS3953; BS3905 and BS3907 transduced with PBS-1 lysate from BS3884; BS3903 and BS3914 transduced with PBS-1 lysate from BS3887; BS3981-83 transduced with PBS-1 lysate from BS3912; BS3890 transduced with PBS-1 lysate from BS3840; BS3880 and BS2882 transduced with PBS-1 lysate from BS3844; BS3850 and BS3851 transduced with PBS-1 lysate from BS3817; BS5026 and BS5041 transduced with PBS-1 lysate from BS3944; BS3853 transduced with PBS-1 lysate from BS3831; BS3897 and BS3956 transduced with lysate from BS3874.

Most of the strains were tested for riboflavin production in shake flasks as described above. After 48 h, riboflavin of a 500 µl sample was dissolved by addition of NaOH, neutralized and after centrifugation the riboflavin concentration of the processed samples was determined by HPLC together with the concentration of DMRL and oxolumazine. For calculation of the riboflavin yield on carbon source, the starting and the residual concentration of all carbon sources were determined by HPLC. The results are shown in Table 3.

TABLE 3A

Riboflavin production with transformed *B. subtilis* strains as indicated based on the wt strain *B. subtilis* 1A747 carrying the native rib leader. The yield is given as g riboflavin per g carbon source (for more explanation see text).

| Strain | Rib leader mutation | Yield [%] |
|---|---|---|
| 1A747 | wild-type | 0.0004 |
| BS3811 | $P_{veg}$ | 0.0120 |
| BS3817 | $P_{Spo15}$ | 0.0163 |
| BS3953 | $P_{veg}$_RK1a | 0.1600 |
| BS3884 | $P_{Spo15}$_RK1a | 0.7706 |
| BS3887 | $P_{veg}$_RK41 | 0.3757 |
| BS3912 | $P_{veg}$_triple ribO | 1.0900 |
| BS3840 | $P_{veg}$_del flank-right | 0.0748 |
| BS3831 | $P_{Spo15}$_del flank-right | 0.0702 |
| BS3844 | $P_{veg}$_del terminator | 0.0666 |
| BS3871 | $P_{Spo15}$_del terminator | 0.0359 |
| BS3874 | $P_{Spo15}$_SWITCH deletion | 0.2823 |
| BS3944 | $P_{Spo15}$_leader deletion | 0.1150 |

TABLE 3B

Riboflavin production with transduced *B. subtilis* strains as indicated based on the riboflavin-overproducing strain *B. subtilis* RB50 carrying the native rib leader. The yield is given as g riboflavin per g carbon source (for more explanation see text).

| Strain | Rib leader mutation | Yield [%] |
|---|---|---|
| RB50 | wild-type rib operon | 0.46 |
| BS3849 | $P_{veg}$ | 1.33 |
| BS3850, BS3851 | $P_{Spo15}$ | 1.57 |
| BS3970, BS3971 | $P_{veg}$_RK1a | 2.88 |
| BS3905, BS3907 | $P_{Spo15}$_RK1a | 3.31 |
| BS3903, BS3914 | $P_{veg}$_RK41 | 4.18 |
| BS3981 | $P_{veg}$_triple ribO | 2.52 |
| BS3890 | $P_{veg}$_del flank-right | 1.14 |
| BS3853 | $P_{Spo15}$_del flank-right | 1.63 |
| BS3880 | $P_{veg}$_del terminator | 1.80 |
| BS3875 | $P_{Spo15}$_del terminator | 2.38 |
| BS3897 | $P_{Spo15}$_SWITCH deletion | 3.76 |
| BS5026 | $P_{Spo15}$_leader deletion | 2.16 |

All manipulation done to the rib leader or to the rib promoter led to an increased riboflavin production. In accordance to the results described in Example 2 (see Table 2), the ribO mutation RK41 was also the most effective one when replacing the native promoter by a stronger, constitutive one. By using a strong promoter a yield of up to 4.2% was reached with the combination of $P_{veg}$ with RK41. Surprisingly, the combination of $P_{Spo15}$ with SWITCH deletion showed the next best yield with 3.8%, which is much better than the combination $P_{Spo15}$ with del terminator that resulted in a yield of 2.4%.

Example 4

Combination of ribO Mutations with Leader Deletions and Replacement of the Native Rib Promoter by Strong Constitutive Promoters To see whether the combination of a typical deregulating ribO mutation with leader deletions is able to increase riboflavin production, some of the mutations generated in Example 2 and 3 were combined. The construction followed the protocol outlined above. Templates and primer pairs for the flank 5' and 3' PCRs are shown in Table 4 (for more information see also Example 1). Assembling PCR and transformation into BS3813 were done as described in Example 2 and 3. Sequencing revealed that two additional mutations were present in constructs $P_{Spo15}$_triple ribO_del mro175 and $P_{veg}$_triple ribO_del mro175, namely T25G and C101T, wherein the numbering relates to SEQ ID NO:42. The designation of the new strains carrying the newly generated constructs is shown in Table 4, column 4.

PBS-1 lysates from the newly generated strains were prepared and used for transduction of BS3798 (generated in Example 1). Selection of transduced cells on SMM plates were performed as described in Example 2. The newly transduced strains were named as indicated in Table 4, column 5.

TABLE 4

Primer pairs used for construction of flank 5' and flank 3' fragments, respectively, resulting in modified rib leader sequences combined with the respective constitutive promoters and the designation of the resulting strains either transformed with said PCR-fragments or transduced with the respective lysates (for more explanation see text).

| Designation of rib leader mutation (Template for PCR) | Flank 3' primer pair (SEQ ID NOs) | Flank 5' primer pair (SEQ ID NOs) | Trans-formed strains | Trans-duced strains |
|---|---|---|---|---|
| $P_{veg}$_triple ribO_del mro175 (BS3912) | p45/p81a (5/29) | p80a/p51 (27/7) | BS3889 | BS3908 |
| $P_{Spo15}$_triple ribO_del mro175 (BS3889) | p45/p63 (5/15) | p62/p51 (14/7) | BS3923 | BS3922 |
| $P_{Spo15}$_RK41_del terminator (BS3871) | p45/p73 (5/18) | p72/p51 (16/7) | BS3954 | BS3984 |
| $P_{Spo15}$_RK41_SWITCH deletion (BS3874) | p45/p73 (5/18) | p72/p51 (16/7) | BS3915 | BS3964 |
| $P_{veg}$_RK41_SWITCH deletion (BS3887) | p45/p81 (5/28) | p80/p51 (26/7) | BS3920 | BS3899 |

Testing of the newly generated strains for riboflavin production was performed via shake flask screening a described above. The results are presented in Table 5 showing a further increase in riboflavin production compared to the results presented in Example 3 (see Table 4). The combination of ribO mutations RK41 and triple ribO, respectively, with a strong promoter and a rib leader deletion resulted in riboflavin yields of more than 7.6% in a shake-flask screening compared to 4.2% achieved with the combination of the $P_{veg}$ promoter with ribO mutation RK41 (see Table 4), the best combination without a leader deletion. The specific leader deletion as described herein did nearly double the yield of deregulated (ribO mutation, constitutive promoter) rib leader-promoter combinations. Besides the "SWITCH deletion" also "del mro175" was unexpectedly able to improve the riboflavin yield in a RB50 background over a construct without deletion. The deletion of the terminator ("del terminator") had also a positive but less pronounced effect. The leader deletion construct in which $P_{spo15}$ is put directly in front of the Shine-Dalgarno sequence of ribD showed a 3.6-times smaller yield than the best triple constructs (BS5026, see Table 4 and 6). These results suggest that the rib leader is not only required for regulation but also for stabilization of the full-length transcript.

TABLE 5

Riboflavin production with transduced B. subtilis strains as indicated based on the riboflavin-overproducing strain B. subtilis RB50 carrying the native rib leader. The yield is given as g riboflavin per g carbon source (for more explanation see text).

| Strain | Rib leader mutation | Yield [%] |
|---|---|---|
| RB50 | wild-type rib operon | 0.46 |
| BS3908 | $P_{veg}$ _triple ribO_del mro175 | 6.79 |
| BS3922 | $P_{Spo15}$ _triple ribO_del mro175 | 6.47 |
| BS3984 | $P_{Spo15}$ _RK41_del terminator | 5.24 |
| BS3964 | $P_{Spo15}$ _RK41_SWITCH deletion | 7.80 |
| BS3899 | $P_{veg}$ _RK41_SWITCH deletion | 7.67 |
| BS5026 | $P_{Spo15}$ _leader deletion | 2.16 |

Example 5

Replacing the Native Rib Leader by an mRNA Stabilizing Element

The DNA sequence of the aprE mRNA stabilizing element was distributed over two PCR products. For amplifying PCR product 1 containing the 5' region of the rib operon at the 5' end of the aprE mRNA stabilizing element, the primers p45 together with p143' (SEQ ID NO:33) and the chromosomal DNA from strain BS3817 as template was used under standard PCR conditions. For amplifying PCR product 2 containing the ribD at the 3' end of the aprE mRNA stabilizing element, the primers p51 together with p142 (SEQ ID NO:32) and the chromosomal DNA from strain BS3817 as template were used under standard PCR conditions. In the standard LFH-PCR reaction, the gel-purified PCR products 1 and 2 were assembled into one DNA fragment as described before. The same method was applied to the grpE mRNA stabilizing element with chromosomal DNA from strain BS3817 as template using primer pair p45/p145' (SEQ ID NO:35) and primer pair p51/p144 (SEQ ID NO:34) for the first two PCRs followed by the assembling PCR using the primer pair p45/p51 under the conditions as described above. The purified LFH-PCR products were transformed again into competent cells of the riboflavin-auxotroph B. subtilis BS3813, in which the riboflavin promoter region and the 5' part of ribD was replaced by a neomycin resistance cassette. Riboflavin-prototroph transformants were selected on SMM plates. Isolated transformants were suspended in 1 ml 0.9% NaCl solution and 100 µl of the 500-fold dilution of the original cell suspension was plated on TBAB agar plates. Single colonies were transferred onto fresh TBAB agar plates and TBAB agar plates supplemented with 2 mg/l Nm and 100 mg/l riboflavin. The correct transformants grew only on TBAB agar plates and were therefore neomycin-sensitive. In addition, the genotype was confirmed by sequencing of the newly introduced stretch of DNA. The resulting strains were designated as BS5193 (carrying the construct $P_{15\Omega aprE}$ribDEAHT) and BS5196 (carrying the construct $P_{15\Omega grpE}$ribDEAHT), respectively.

PBS-1 lysates from strains BS5193 and BS5196 were prepared and used for transduction of BS3798 (generated in Example 1). Selection of transduced cells on SMM plates were performed as described in Example 2. The newly transduced strains based on strain BS5193 were named BS5260 and BS5262, respectively, the newly transduced strain based on strain BS5196 was named BS5244.

Riboflavin production was tested in shake flask experiments as described above. The results are shown in Table 6.

TABLE 6A

Riboflavin production with transformed B. subtilis strains as indicated compared to the wt B. subtilis strain 1A747 carrying the native rib leader. The yield is given as g riboflavin per g carbon source (for more explanation see text).

| Strain | Rib leader mutation | Yield [%] |
|---|---|---|
| 1A747 | wild-type | 0.0004 |
| BS3817 | $P_{Spo15}$ | 0.0163 |
| BS3944 | $P_{Spo15}$ _leader deletion | 0.1150 |
| BS5193 | $P_{Spo15}$ _aprE | 0.1000 |
| BS5196 | $P_{Spo15}$ _grpE | 0.3700 |

TABLE 6B

Riboflavin production of transduced B. subtilis strains as indicated compared to the riboflavin-overproducing strain B. subtilis RB50 carrying the native rib leader. The yield is given as g riboflavin per g carbon source (for more explanation see text).

| Strain | Rib leader mutation | Yield [%] |
|---|---|---|
| RB50 | wild-type rib operon | 0.46 |
| BS3850 | $P_{Spo15}$ | 1.57 |
| BS5026 | $P_{Spo15}$ _leader deletion | 2.16 |
| BS5260 | $P_{Spo15}$ _aprE | 2.07 |
| BS5244 | $P_{Spo15}$ _grpE | 2.99 |

Replacing the rib promoter by a non-regulated constitutive promoter like $P_{Spo15}$ increased the riboflavin yield in the shake-flask screening compared to a regulated wild-type rib operon 41-fold in a wild-type background and 3.4-fold in a RB50 background. When the rib leader was removed and the $P_{Spo15}$ promoter was put directly in front of ribD, the riboflavin yield was again 7-fold increased in a wild-type host strain and 1.4-fold in the RB50 background. Replacing the rib leader by the aprE mRNA stabilizing element showed no influence on the yield in the two strain backgrounds used above. However, by replacing the rib leader with the grpE mRNA stabilizing element, the riboflavin yield was 3.7-fold increased in a wild-type host and 1.44-fold in the RB50 background.

In order to check the influence of the host strain with regards to the performance of a modified rib operon, the lysates from B. subtilis 1A747 (wild-type rib operon), BS5193, BS5196 and BS3944 were also transduced into another RB50 variant named BS5178 (spo0A⁻, rib::neo, ribC1, bpr::cam, tkt$^{mut}$). Shake flask screenings were performed as described above. The results including the names of the newly constructed strains are shown in Table 7.

TABLE 7

Riboflavin production of transduced B. subtilis strains as indicated above. The yield is given as g riboflavin per g carbon source and compared to the yield of BS5240.

| Strain | Rib leader mutation | Yield [%] |
| --- | --- | --- |
| BS5240 | $P_{Spol5}$_leader deletion | 100 |
| BS5191 | wild-type rib operon | 40 |
| BS5237 | $P_{Spol5}$_aprE | 140 |
| BS5238 | $P_{Spol5}$_grpE | 270 |

In the new strain background the positive effect of the stabilizing elements was more pronounced when tested in the shake flask format. Now, the aprE mRNA stabilizing element, too, increased the riboflavin yield by 40% compared to a strain carrying the rib operon without a leader. The grpE mRNA stabilizing element even showed a 2.7-fold increased yield compared to the construct without a rib leader.

In the new strain background the positive effect of the stabilizing elements was more pronounced when tested in the shake flask format. Now, the aprE mRNA stabilizing element, too, increased the riboflavin yield by 40% compared to a strain carrying the rib operon without a leader. The grpE mRNA stabilizing element even showed a 2.7-fold increased yield compared to the construct without a rib leader.

Example 6

Combination of Additional ribO Mutations with Leader Deletions and Strong Constitutive Promoters In the same way as the ribO mutations RK41 (=RK61a), RK1a and "triple ribO", which combines the ribO mutations RK4, RK8, RK5 (=RK2) of Kil et al., 1992, were introduced into the rib leader, additional ribO mutation described in Kil et al., 1992, can be used for the generation of alternative optimized rib leaders. Numbering of the mutations refers to the rib leader sequence shown in SEQ ID NO:42. The described mutations RK111a (G59A), RK116a (G56A), RK62a (G60A; identical to RK82a), RK93a (C87T), and RK27a (C128T) are combined with del terminator, the SWITCH deletion and del mro175 (see above) together with a strong constitutive promoter $P_{Spo15}$ or $P_{veg}$ depending on the template used for generation of flank 5' and flank 3'. Any mutation effective as ribO mutation can be combined in this way with the described promoters and leader deletions.

The following primer pairs are used for construction of the ribO mutations: primer pair p111a_f/p 111a_r (SEQ ID NO:83 and 84) for construction of RK111a, primer pair p116a_f/p116a_r (SEQ ID NO:85 and 86) for construction of RK116a, primer pair p62a_f/p62a_r (SEQ ID NO:87 and 88) for construction of RK62a, primer pair p93a_f/p93a_r (SEQ ID NO:89 and 90) for construction of RK93a, and primer pair p27a_f/p27a_r (SEQ ID NO:91 and 92 for construction of RK27a. These primers are used in PCR-reactions as described in Example 2. For generation of flank 5', primer p45 is applied together with the antisense primer. For generation of flank 3', the sense primer is applied together with primer p51. Flank 5' and 3' are assembled in a third PCR using primers p45 and p51 (see Example 2). Transformation and transduction of strains are performed as described in Example 2. For the replacement of the native promoter the instructions according to Example 3, for combination of ribO mutations with leader mutations the instructions according to Example 4 are followed.

TABLE 9

Templates required for generation of the ribO constructs by the PCR-based method as described above in the previous examples (for more explanation see text).

| Designation of rib leader mutation | Template for flank 5' | Template for flank 3' |
| --- | --- | --- |
| $P_{Spol5}$_RK111a | BS3817 | BS3817 |
| $P_{veg}$_RK111a | BS3811 | BS3811 |
| $P_{Spol5}$_RK111a_SWITCH deletion | BS3874 | BS3874 |
| $P_{veg}$_RK111a_SWITCH deletion | BS3811 | BS3867 |
| $P_{Spol5}$_RK111a_del terminator | BS3871 | BS3871 |
| $P_{veg}$_RK111a_del terminator | BS3844 | BS3844 |
| $P_{Spol5}$_RK111a_del mro175 | BS3817 | BSmro175 |
| $P_{veg}$_RK111a_del mro175 | BS3811 | BSmro175 |

The generated PCR products for all constructs listed in Table 9 are transformed into BS3813. Selection takes place as described in Example 2 and lysates of the confirmed strains are used for transduction of BS3798. The yield of riboflavin obtained in flask shake experiments as described above are in the range as for constructs RK41_SWITCH deletion or triple ribO_del mro175 (see Table 5). These amounts are even increased when using another strain background, as e.g. described in Example 5.

Example 7

Generation of Strains Other than B. subtilis Carrying Modified Rib Leader Sequences The constructs as described in the Examples above can be used to identify/generate corresponding modifications in rib leader sequences from other strains which are known to have a riboswitch in place and which are suitable host strains for riboflavin production.

Corresponding parts of the non-modified rib leaders are identified in other organisms according to the alignment depicted in FIG. 2 of Vitreschak et al., Nucleic Acid Res 30, 3141-3151, 2002. Deletion mutations are generated as described above and optionally combined with ribO mutations (homologous to the ones identified in B. subtilis). The constructs can be furthermore combined with strong promoters or other known modification of the host strain as described above in order to increase riboflavin production under suitable culture conditions which are known to the skilled person.

The invention claimed is:

1. A mutated Bacillus subtilis rib leader sequence of the riboflavin biosynthesis operon operatively linked to at least one downstream rib gene,
wherein said mutated Bacillus subtilis rib leader sequence does not comprise a Bacillus subtilis rib leader terminator sequence and does comprise at least one ribO mutation,
wherein said Bacillus subtilis rib leader terminator sequence consists of a contiguous sequence of nucleotides 231-263 of SEQ ID NO: 42, and said at least one ribO mutation is selected from the group consisting of a mutation of one of the following positions of SEQ ID NO:42: T31, G39, G40, G41, C55, C85, C86, G88, C93, A116, G121 and C128.

2. A mutated *Bacillus subtilis* rib leader sequence of the riboflavin biosynthesis operon operatively linked to at least one downstream rib gene and a constitutive promoter, wherein said mutated *Bacillus subtilis* rib leader sequence operably linked to a constitutive promoter comprises the nucleotide sequence of SEQ ID NO:67, 68, 69, 70 or 71.

3. The mutated *Bacillus subtilis* rib leader sequence of claim 1 fused to a constitutive promoter.

4. A riboflavin-producing microorganism genetically engineered with a mutated *Bacillus subtilis* rib leader sequence of claim 1.

5. A riboflavin-producing microorganism according to claim 4 capable of producing at least 5% more riboflavin from a given carbon source compared to production of riboflavin using a wild-type microorganism.

6. A riboflavin-producing microorganism according to claim 4 wherein the accumulation of intact, full-length riboflavin mRNA is improved compared to a wild-type microorganism.

7. A method for production of riboflavin comprising culturing a microorganism with a carbon source under conditions whereby riboflavin is produced by said microorganism, said microorganism comprising the mutated *Bacillus subtilis* rib leader sequence of claim 1.

8. A process for the production of a microorganism according to claim 4 comprising the steps of:
(a) providing a microorganism capable of riboflavin production comprising a rib operon including leader sequences; and
(b) genetically engineering said microorganism with a polynucleotide.

9. A process for the production of riboflavin comprising the use of a microorganism according to claim 4 and optionally isolating and/or purifying the produced riboflavin from the reaction mixture.

10. A process according to claim 9 wherein the microorganism is incubated in an aqueous medium under conditions that allow the production of riboflavin from a given substrate.

11. A process for the production of full-length mRNA transcripts from riboflavin biosynthetic genes in a riboflavin-producing microorganism comprising introducing into said microorganism a polynucleotide according to claim 1.

12. The modified polynucleotide sequence according to claim 3 wherein the constitutive promoter is selected from $P_{veg}$ or $P_{Spo15}$.

13. A mutated Bacillus subtilis rib leader sequence of the riboflavin biosynthesis operon operatively linked to at least one downstream rib gene,
wherein said mutated Bacillus subtilis rib leader sequence does not comprise a Bacillus subtilis rib leader terminator sequence and does comprise at least one ribO mutation,
wherein said Bacillus subtilis rib leader terminator sequence consists of a contiguous sequence of nucleotides 231-263 of SEQ ID NO:42, and said at least one ribO mutation is selected from the group consisting of a mutation of one of the following positions of SEQ ID NO:42: T31, G39, G40, G41, C55, C85, C86, G88, C93, A116, G121 and C128, and
wherein said mutated rib leader sequence leads to relaxation or reduction of a repressive effect of a non-modified Bacillus subtilis rib leader sequence on expression of a downstream rib gene when said mutated rib leader sequence is expressed in a riboflavin biosynthesis operon as compared to expression of said non-modified Bacillus subtilis rib leader sequence in the riboflavin biosynthesis operon.

14. A mutated Bacillus subtilis rib leader sequence of the riboflavin biosynthesis operon operatively linked to at least one downstream rib gene, wherein said mutated Bacillus subtilis rib leader sequence does not comprise a Bacillus subtilis rib leader terminator sequence and does comprise at least one ribO mutation, wherein said Bacillus subtilis rib leader terminator sequence consists of a contiguous sequence of nucleotides 231-263 of SEQ ID NO:42, and said at least one ribO mutation is selected from the group consisting of a mutation of one of the following positions of SEQ ID NO:42: G39, G40, G41, C85 and G121.

* * * * *